(12) United States Patent
Douglas

(10) Patent No.: US 10,776,989 B1
(45) Date of Patent: Sep. 15, 2020

(54) METHOD AND APPARATUS FOR PRIORITIZED VOLUME RENDERING

(71) Applicant: Robert Edwin Douglas, Winter Park, FL (US)

(72) Inventor: Robert Edwin Douglas, Winter Park, FL (US)

(*) Notice: Subject to any disclaimer, the term of this patent is extended or adjusted under 35 U.S.C. 154(b) by 0 days.

(21) Appl. No.: 16/879,758

(22) Filed: May 21, 2020

Related U.S. Application Data

(63) Continuation-in-part of application No. 16/842,631, filed on Apr. 7, 2020.

(60) Provisional application No. 62/846,770, filed on May 13, 2019.

(51) Int. Cl.
*G06T 15/08* (2011.01)
*G06T 7/00* (2017.01)
*G06T 19/20* (2011.01)
*G06T 5/00* (2006.01)
*G06T 15/20* (2011.01)
*G16H 30/40* (2018.01)

(52) U.S. Cl.
CPC .............. *G06T 15/08* (2013.01); *G06T 5/008* (2013.01); *G06T 7/0012* (2013.01); *G06T 15/20* (2013.01); *G06T 19/20* (2013.01); *G16H 30/40* (2018.01); *G06T 2200/04* (2013.01); *G06T 2207/10081* (2013.01); *G06T 2207/20092* (2013.01); *G06T 2207/30012* (2013.01); *G06T 2207/30096* (2013.01); *G06T 2210/41* (2013.01); *G06T 2219/2016* (2013.01)

(58) Field of Classification Search
CPC .............................. G16H 50/20; G16H 30/40
See application file for complete search history.

(56) References Cited

U.S. PATENT DOCUMENTS

| 7,830,381 | B2* | 11/2010 | Lundstrom | G06T 15/08 |
| | | | | 345/424 |
| 9,980,691 | B2* | 5/2018 | Douglas | A61B 6/462 |
| 2013/0011038 | A1* | 1/2013 | Eda | A61B 8/485 |
| | | | | 382/131 |
| 2013/0039552 | A1* | 2/2013 | Becker | G06F 19/321 |
| | | | | 382/128 |
| 2014/0257854 | A1* | 9/2014 | Becker | G06F 19/321 |
| | | | | 705/3 |
| 2019/0156937 | A1* | 5/2019 | Shimomura | G16H 10/40 |
| 2019/0228524 | A1* | 7/2019 | Chen | G16H 30/20 |
| 2020/0058390 | A1* | 2/2020 | Kohle | G06K 9/00208 |

* cited by examiner

Primary Examiner — Ross Varndell

(57) ABSTRACT

In this patent, a method for prioritizing items within a 3D volume is presented. This allows prioritized items within the display to achieve preferential display. Augmented visualization strategies of such prioritized items are also provided.

18 Claims, 36 Drawing Sheets

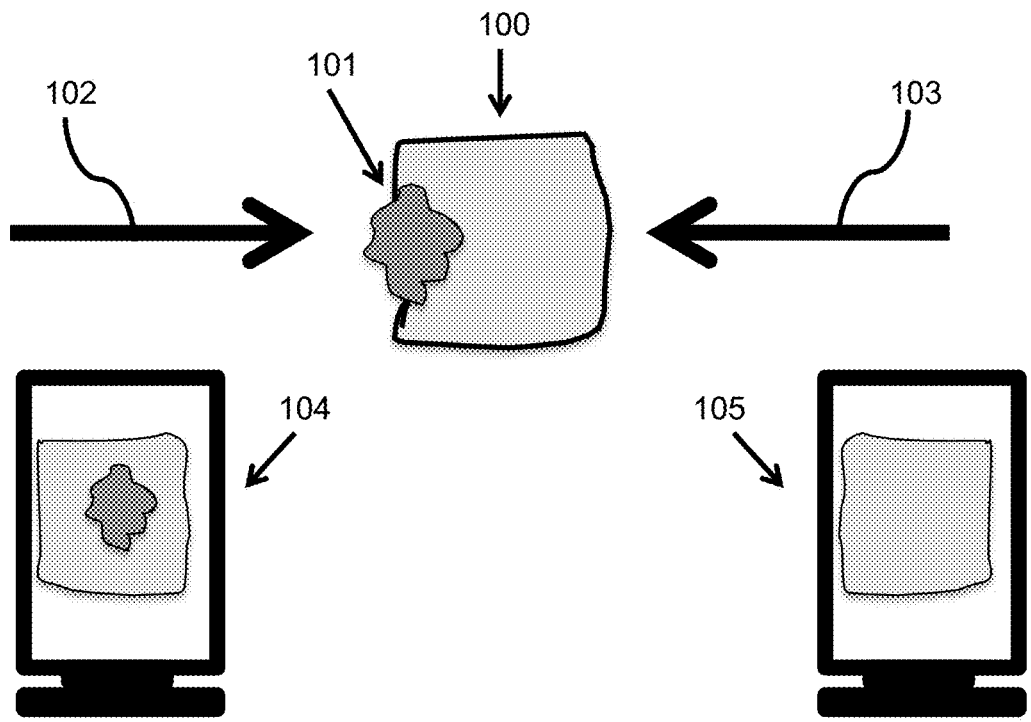
Fig. 1A PRIOR ART OF VOLUME RENDERING
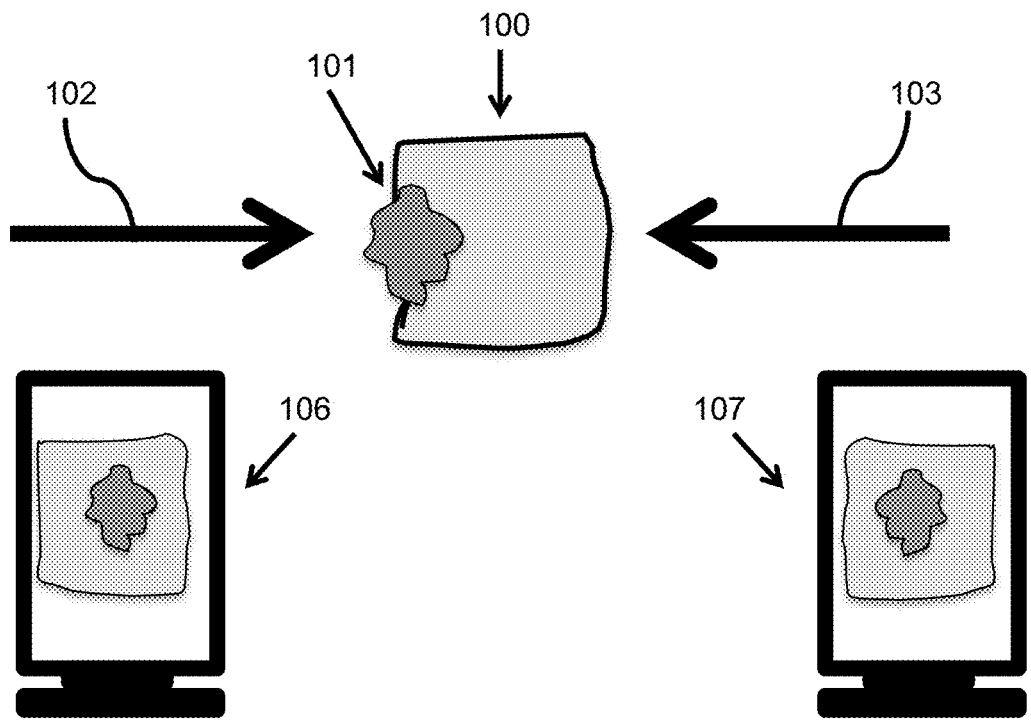
Fig. 1B PATENT METHOD OF PRIORITIZED VOLUME RENDERING

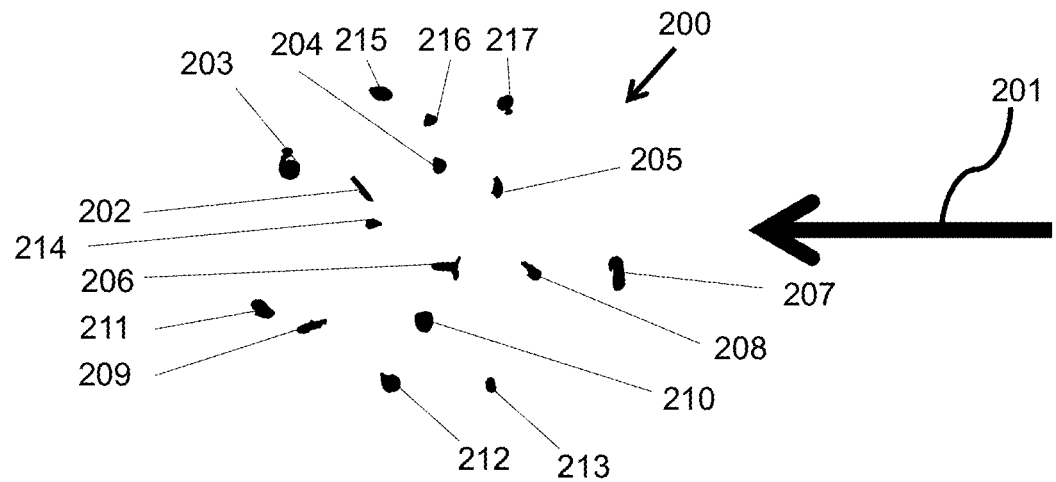
Fig. 2A CLUSTER OF MICROCALCIFICATIONS
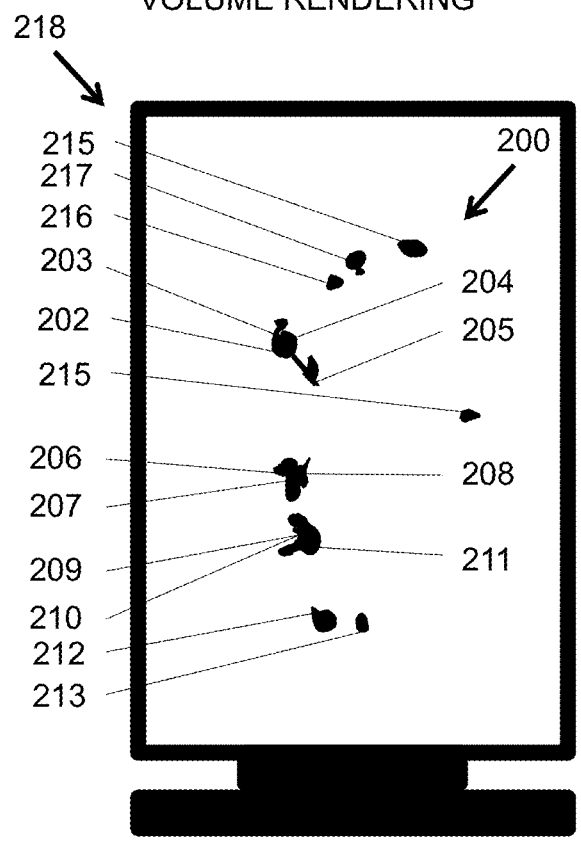
Fig. 2B PRIOR ART OF CONVENTIONAL VOLUME RENDERING
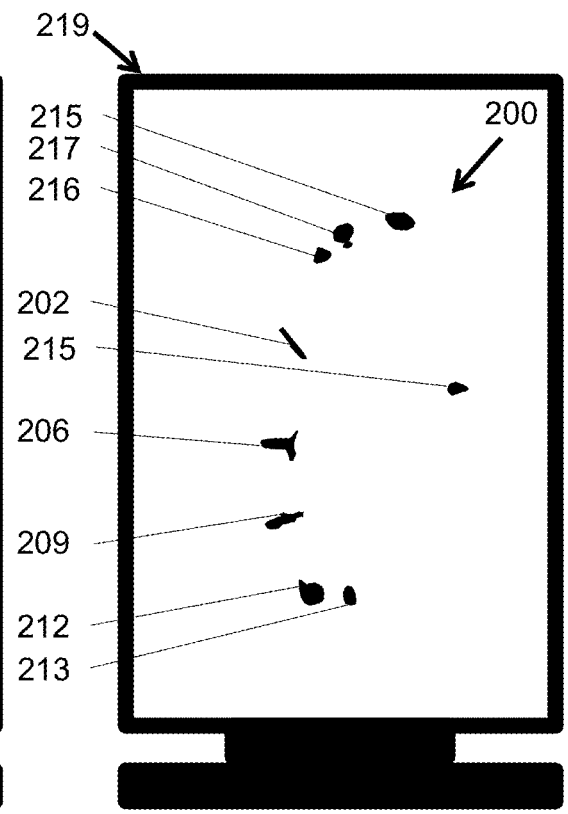
Fig. 2C PATENT METHOD OF PRIORITIZED VOLUME RENDERING

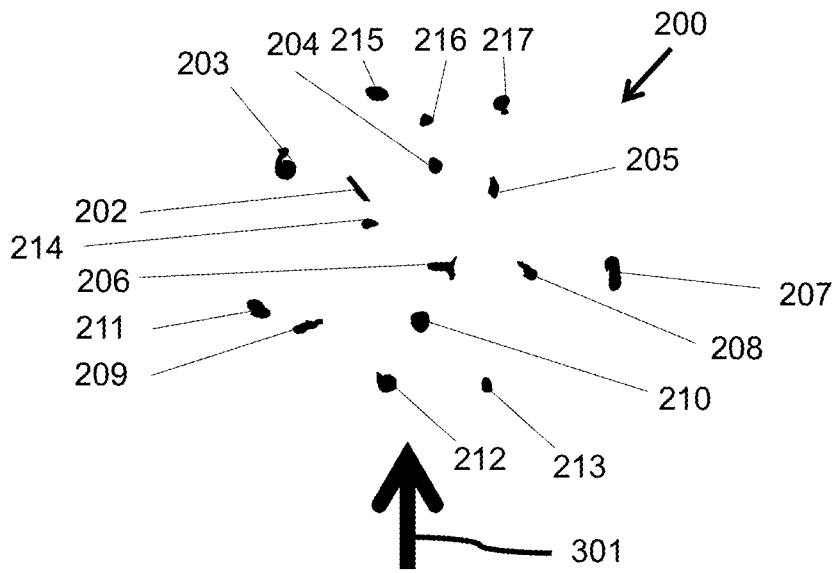
Fig. 3A CLUSTER OF MICROCALCIFICATIONS
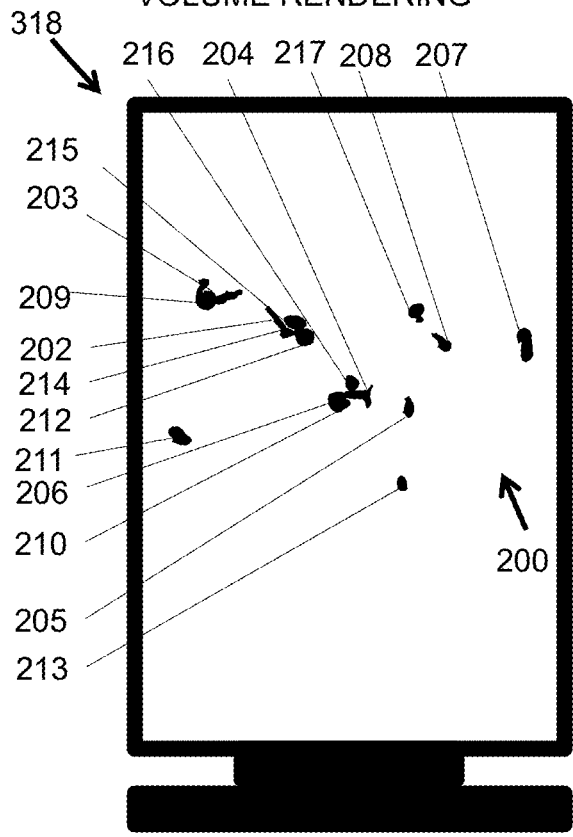
Fig. 3B PRIOR ART OF CONVENTIONAL VOLUME RENDERING
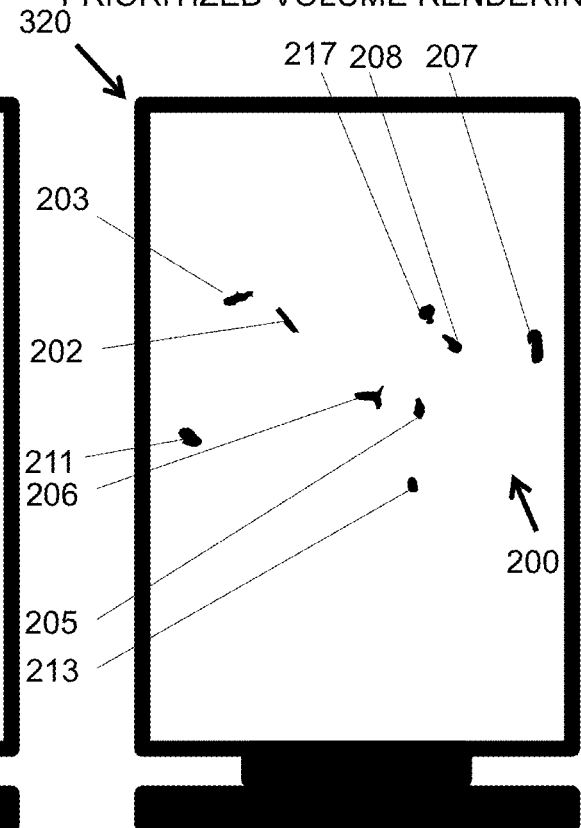
Fig. 3C PATENT METHOD OF PRIORITIZED VOLUME RENDERING

Fig. 16A

| -80 | -78 | -89 | -86 | -80 | -80 | -87 | -80 | -87 | -80 |
|-----|-----|-----|-----|-----|-----|-----|-----|-----|-----|
| -78 | -82 | -88 | -87 | 170 | 183 | -87 | -78 | -80 | -78 |
| -83 | -80 | 175 | 180 | 156 | 188 | 182 | 186 | -80 | -80 |
| -86 | -83 | 170 | 181 | 181 | 189 | 36  | 188 | -83 | -82 |
| -90 | -86 | 172 | 183 | 177 | 39  | 176 | 182 | 189 | -83 |
| -78 | -87 | 168 | 181 | 171 | 34  | 174 | 188 | 194 | -82 |
| -75 | -82 | 166 | 178 | 190 | 39  | 180 | 179 | 190 | -80 |
| -80 | -90 | 165 | 177 | 189 | 40  | 176 | 184 | -81 | -90 |
| -90 | -87 | -89 | 165 | 184 | 190 | 41  | 190 | -79 | -86 |
| -89 | -87 | -82 | -82 | -80 | -82 | -81 | -92 | -76 | -90 |

Fig. 16B

| 1 | 1 | 1 | 1 | 1  | 1 | 1 | 1 | 1 | 1 |
|---|---|---|---|----|---|---|---|---|---|
| 1 | 1 | 1 | 1 | 1  | 1 | 1 | 1 | 1 | 1 |
| 1 | 1 | 1 | 1 | 1  | 1 | 1 | 1 | 1 | 1 |
| 1 | 1 | 1 | 1 | 1  | 1 | 1 | 1 | 1 | 1 |
| 1 | 1 | 1 | 1 | 10 | 1 | 1 | 1 | 1 | 1 |
| 1 | 1 | 1 | 1 | 1  | 1 | 1 | 1 | 1 | 1 |
| 1 | 1 | 1 | 1 | 1  | 1 | 1 | 1 | 1 | 1 |
| 1 | 1 | 1 | 1 | 1  | 1 | 1 | 1 | 1 | 1 |
| 1 | 1 | 1 | 1 | 1  | 1 | 1 | 1 | 1 | 1 |
| 1 | 1 | 1 | 1 | 1  | 1 | 1 | 1 | 1 | 1 |

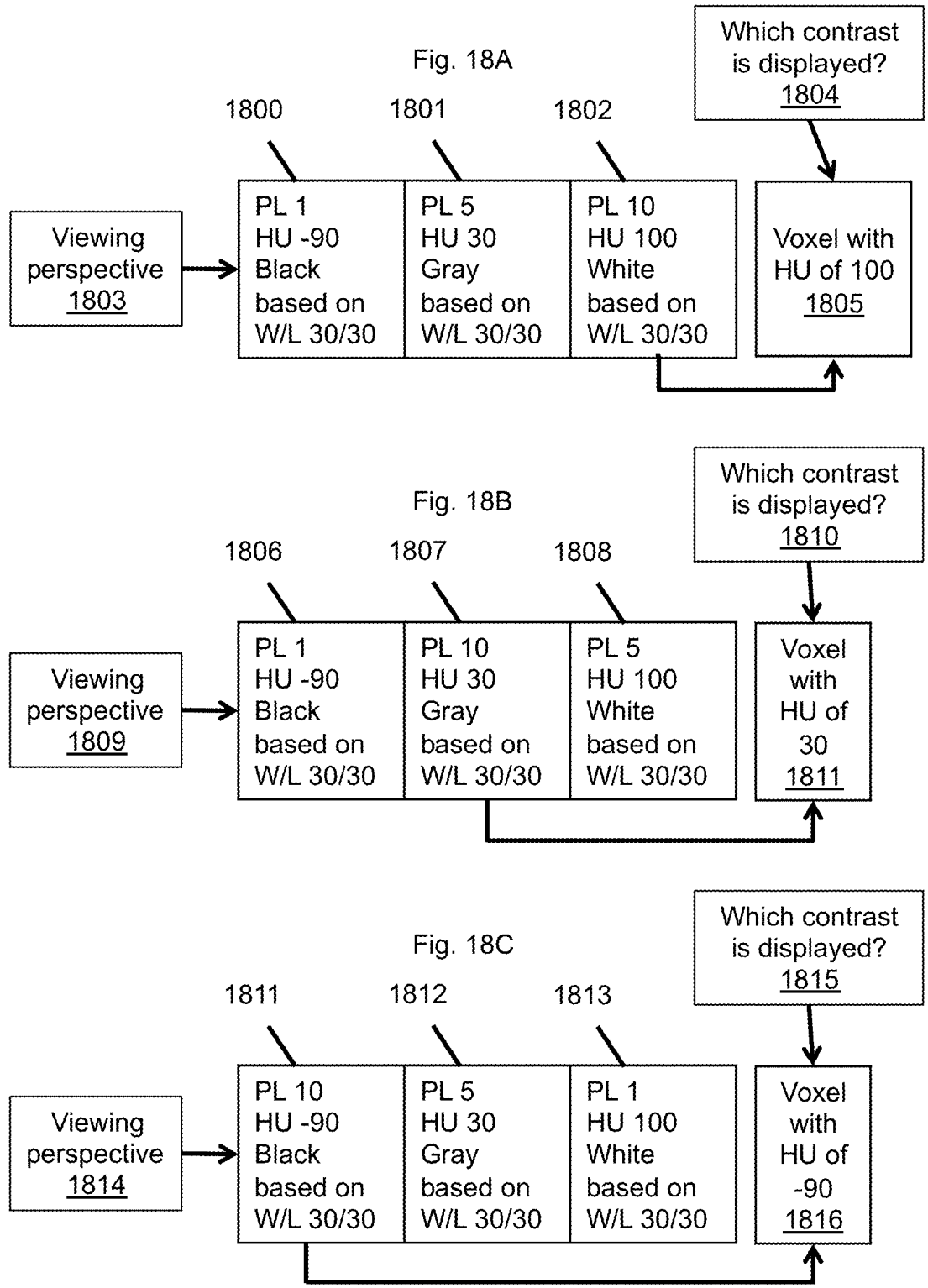

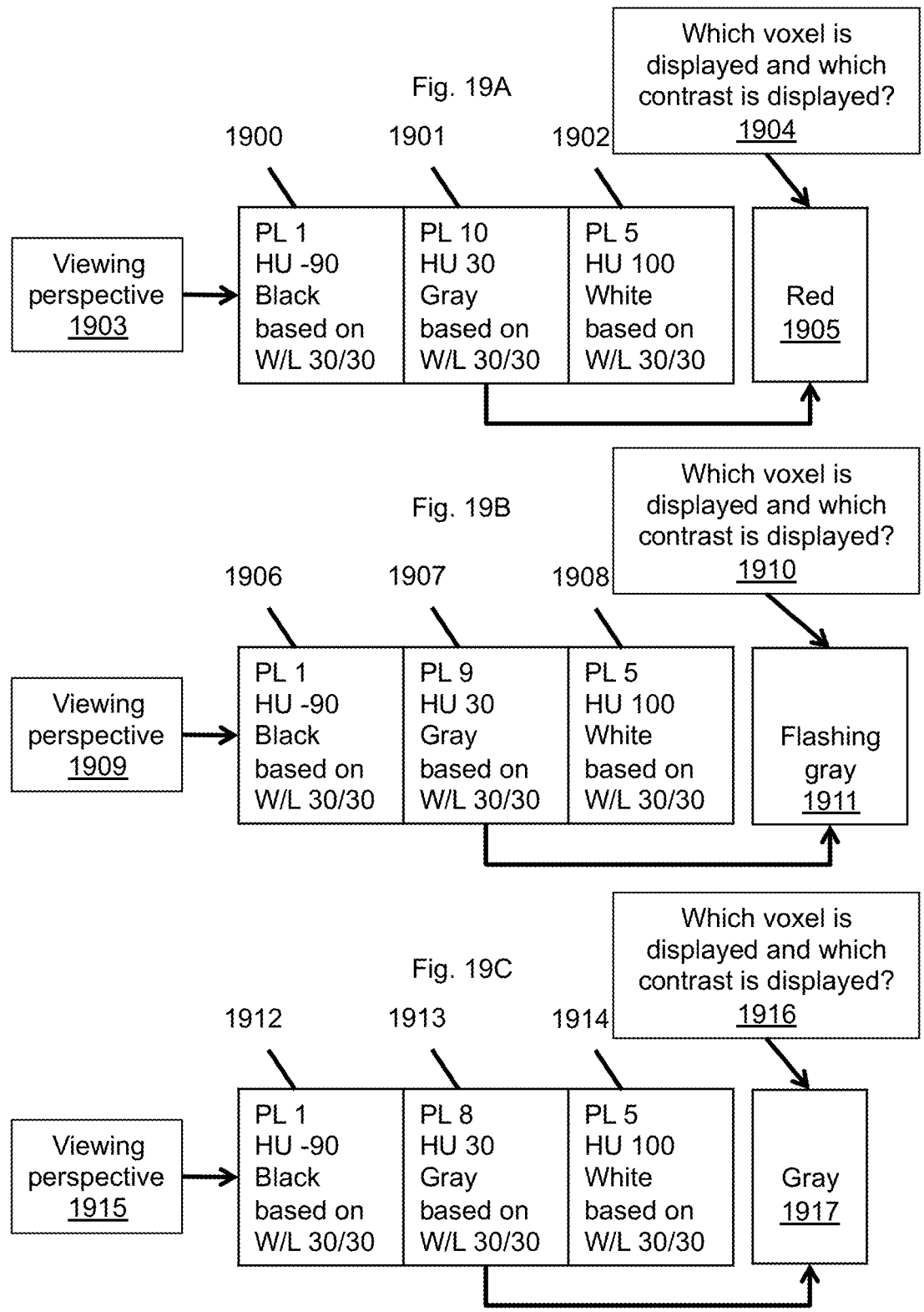

Fig. 20A

| -80 | -78 | -89 | -86 | -80 | -80 | -87 | -80 | -87 | -80 |
|---|---|---|---|---|---|---|---|---|---|
| -78 | -82 | -88 | -87 | 170 | 183 | -87 | -78 | -80 | -78 |
| -83 | -80 | 175 | 180 | 156 | 188 | 182 | 186 | -80 | -80 |
| -86 | -83 | 170 | 181 | 181 | 189 | 36 | 188 | -83 | -82 |
| -90 | -86 | 172 | 183 | 177 | 39 | 176 | 182 | 189 | -83 |
| -78 | -87 | 168 | 181 | 171 | 34 | 174 | 188 | 194 | -82 |
| -75 | -82 | 166 | 178 | 190 | 39 | 180 | 179 | 190 | -80 |
| -80 | -90 | 165 | 177 | 189 | 40 | 176 | 184 | -81 | -90 |
| -90 | -87 | -89 | 165 | 184 | 190 | 41 | 190 | -79 | -86 |
| -89 | -87 | -82 | -82 | -80 | -82 | -81 | -92 | -76 | -90 |

Fig. 20B

| 1 | 1 | 1 | 1 | 1 | 1 | 1 | 1 | 1 | 1 |
|---|---|---|---|---|---|---|---|---|---|
| 1 | 1 | 1 | 1 | 5 | 5 | 1 | 1 | 1 | 1 |
| 1 | 1 | 5 | 5 | 5 | 5 | 5 | 5 | 1 | 1 |
| 1 | 1 | 5 | 5 | 5 | 5 | 10 | 5 | 1 | 1 |
| 1 | 1 | 5 | 5 | 5 | 10 | 5 | 5 | 5 | 1 |
| 1 | 1 | 5 | 5 | 5 | 10 | 5 | 5 | 5 | 1 |
| 1 | 1 | 5 | 5 | 5 | 10 | 5 | 5 | 5 | 1 |
| 1 | 1 | 5 | 5 | 5 | 10 | 5 | 5 | 1 | 1 |
| 1 | 1 | 1 | 5 | 5 | 5 | 10 | 5 | 1 | 1 |
| 1 | 1 | 1 | 1 | 1 | 1 | 1 | 1 | 1 | 1 |

Fig. 21A

| -80 | -78 | -89 | -86 | -80 | -80 | -87 | -80 | -87 | -80 |
|-----|-----|-----|-----|-----|-----|-----|-----|-----|-----|
| -78 | -82 | -88 | -87 | 170 | 183 | -87 | -78 | -80 | -78 |
| -83 | -80 | 175 | 180 | 156 | 188 | 182 | 186 | -80 | -80 |
| -86 | -83 | 170 | 181 | 181 | 189 | 36  | 188 | -83 | -82 |
| -90 | -86 | 172 | 183 | 177 | 39  | 176 | 182 | 189 | -83 |
| -78 | -87 | 168 | 181 | 171 | 34  | 174 | 188 | 194 | -82 |
| -75 | -82 | 166 | 178 | 190 | 39  | 180 | 179 | 190 | -80 |
| -80 | -90 | 165 | 177 | 189 | 40  | 176 | 184 | -81 | -90 |
| -90 | -87 | -89 | 165 | 184 | 190 | 41  | 190 | -79 | -86 |
| -89 | -87 | -82 | -82 | -80 | -82 | -81 | -92 | -76 | -90 |

Fig. 21B

| 10 | 10 | 10 | 1 | 1 | 1 | 1 | 1 | 1 | 1 |
|----|----|----|---|---|---|---|---|---|---|
| 10 | 10 | 10 | 1 | 1 | 1 | 1 | 1 | 1 | 1 |
| 10 | 10 | 10 | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |
| 1  | 1  | 1  | 1 | 1 | 1 | 1 | 1 | 1 | 1 |

Fig. 22A

| -80 | -78 | -89 | -86 | -80 | -80 | -87 | -80 | -87 | -80 |
|---|---|---|---|---|---|---|---|---|---|
| -78 | -82 | -88 | -87 | 170 | 183 | -87 | -78 | -80 | -78 |
| -83 | -80 | 175 | 180 | 156 | 188 | 182 | 186 | -80 | -80 |
| -86 | -83 | 170 | 181 | 181 | 189 | 36 | 188 | -83 | -82 |
| -90 | -86 | 172 | 183 | 177 | 39 | 176 | 182 | 189 | -83 |
| -78 | -87 | 168 | 181 | 171 | 34 | 174 | 188 | 194 | -82 |
| -75 | -82 | 166 | 178 | 190 | 39 | 180 | 179 | 190 | -80 |
| -80 | -90 | 165 | 177 | 189 | 40 | 176 | 184 | -81 | -90 |
| -90 | -87 | -89 | 165 | 184 | 190 | 41 | 190 | -79 | -86 |
| -89 | -87 | -82 | -82 | -80 | -82 | -81 | -92 | -76 | -90 |

Fig. 22B

| 1 | 1 | 1 | 1 | 1 | 1 | 1 | 1 | 1 | 1 |
|---|---|---|---|---|---|---|---|---|---|
| 1 | 1 | 1 | 1 | 1 | 1 | 1 | 1 | 1 | 1 |
| 1 | 1 | 1 | 1 | 1 | 1 | 1 | 1 | 1 | 1 |
| 1 | 1 | 1 | 1 | 1 | 1 | 1 | 1 | 1 | 1 |
| 1 | 1 | 1 | 1 | 10 | 1 | 1 | 1 | 1 | 1 |
| 1 | 1 | 1 | 1 | 1 | 1 | 1 | 1 | 1 | 1 |
| 1 | 1 | 1 | 1 | 1 | 1 | 1 | 1 | 1 | 1 |
| 1 | 1 | 1 | 1 | 1 | 1 | 1 | 1 | 1 | 1 |
| 1 | 1 | 1 | 1 | 1 | 1 | 1 | 1 | 1 | 1 |
| 1 | 1 | 1 | 1 | 1 | 1 | 1 | 1 | 1 | 1 |

Fig. 23A

| -80 | -78 | -89 | -86 | -80 | -80 | -87 | -80 | -87 | -80 |
|---|---|---|---|---|---|---|---|---|---|
| -78 | -82 | -88 | -87 | 170 | 183 | -87 | -78 | -80 | -78 |
| -83 | -80 | 175 | 180 | 156 | 188 | 182 | 186 | -80 | -80 |
| -86 | -83 | 170 | 181 | 181 | 189 | 36 | 188 | -83 | -82 |
| -90 | -86 | 172 | 183 | 177 | 39 | 176 | 182 | 189 | -83 |
| -78 | -87 | 168 | 181 | 171 | 34 | 174 | 188 | 194 | -82 |
| -75 | -82 | 166 | 178 | 190 | 39 | 180 | 179 | 190 | -80 |
| -80 | -90 | 165 | 177 | 189 | 40 | 176 | 184 | -81 | -90 |
| -90 | -87 | -89 | 165 | 184 | 190 | 41 | 190 | -79 | -86 |
| -89 | -87 | -82 | -82 | -80 | -82 | -81 | -92 | -76 | -90 |

Fig. 23B

| 1 | 2 | 1 | 1 | 1 | 1 | 1 | 1 | 1 | 1 |
|---|---|---|---|---|---|---|---|---|---|
| 2 | 1 | 1 | 1 | 5 | 5 | 1 | 2 | 1 | 2 |
| 1 | 1 | 5 | 5 | 5 | 5 | 5 | 5 | 1 | 1 |
| 1 | 1 | 5 | 5 | 5 | 5 | 10 | 5 | 1 | 1 |
| 1 | 1 | 5 | 5 | 5 | 10 | 5 | 5 | 5 | 1 |
| 2 | 1 | 5 | 5 | 5 | 10 | 5 | 5 | 5 | 1 |
| 2 | 1 | 5 | 5 | 5 | 10 | 5 | 5 | 5 | 1 |
| 1 | 1 | 5 | 5 | 5 | 10 | 5 | 5 | 1 | 1 |
| 1 | 1 | 1 | 5 | 5 | 5 | 10 | 5 | 2 | 1 |
| 1 | 1 | 1 | 1 | 1 | 1 | 1 | 1 | 1 | 1 |

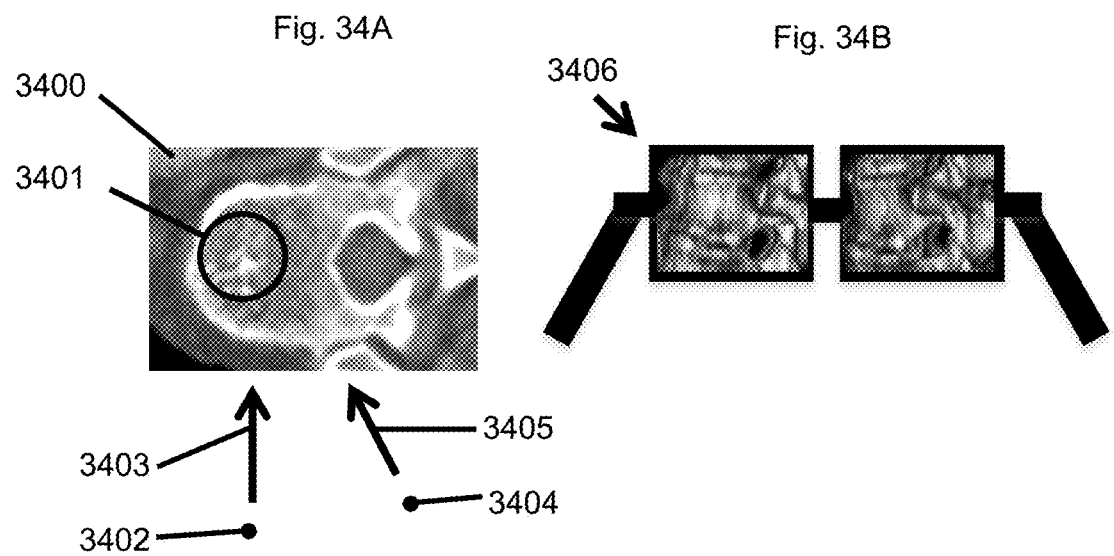
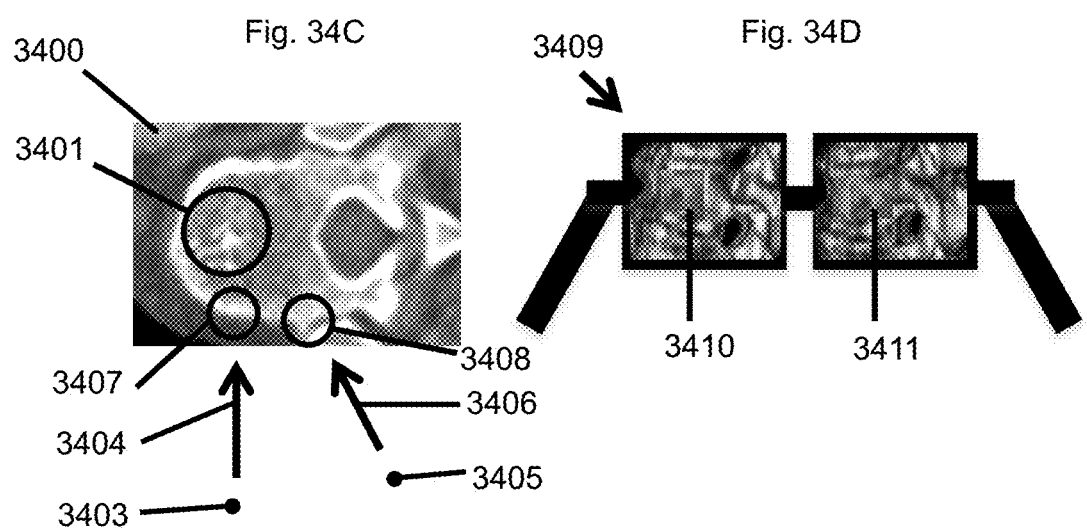

US 10,776,989 B1

METHOD AND APPARATUS FOR PRIORITIZED VOLUME RENDERING

TECHNICAL FIELD

Aspects of this disclosure are generally related to use of 3D visualization.

INTRODUCTION

Volumetric datasets are now commonly being visualized on flat screen monitors, augmented reality head displays and virtual reality head displays. Volumetric datasets are also being sent to 3D printers. Volumetric datasets are being used in the medicine and many other industries.

SUMMARY

All examples, aspects and features mentioned in this document can be combined in any technically conceivable way.

This patent improves upon current visualization strategies. Current volume rendering strategies enable a user to view a structure in a 3D dataset in real time. For example, in the medical field, a user could visualize a vertebrae in the spine from many viewing angles. If there was a small tumor located at the left side of the vertebrae, the user by viewing from multiple angles (e.g., front side, right side, back side) would not see the tumor, but if the user continued to rotate the viewing angle to be viewed from the left side, the tumor would be identified. The current patent improves on this technology because it provides capability of assignment of a priority level score to items (e.g., voxels or segmented structures) and then provides the capability of strategic viewing of prioritized items while also showing the surrounding non-prioritized items so that the user has context. This is useful because dangerous findings could be seen from all angles, not just the optimal viewing angle. In other words, this patent improves upon the current state of the art because dangerous findings that lie deep within the 3D volume would not be hidden by more benign findings that lie more superficially.

By improving visualization of the critical findings of interest, namely dangerous findings that lie deep within the dataset, both efficiency and diagnostic accuracy can be improved over a wide range of scenarios. For example, visualization of dangerous findings such as microcalcifications in the breast and pulmonary nodules, which could be potentially hidden and missed by a radiologist can be seen better by assigning these findings a high priority level and performing prioritize volume rendering discussed herein. Alternatively, visualization of anatomic structures whom have a statistically higher probability of harboring pathology can be seen better by assigning these findings a high priority level and performing prioritize volume rendering discussed herein. Furthermore, certain anatomic structures (e.g., basilar artery tip) that are commonly of interest or can be marked up to be of interest (e.g., use 3D cursor of U.S. Pat. No. 9,980,691) can be allocated a high priority level.

Next, the assignment of priority levels can be discussed. In general, priority levels can be assigned to individual voxels or to groups of voxels (e.g., such as performing segmentation and assigning all voxels within the femur bone the same priority level). In general, priority levels can be assigned based on a numerical scoring system (e.g., 1 to 10) or a categorical scoring system (e.g., high, medium and low).

Next, visualization a high priority structure through a prioritized volume rendering process. This patent is therefore useful in visualizing critical findings in the context of other findings.

In accordance with an aspect a method comprises: augmenting visualization of item(s) within a 3D volume to improve visualization of prioritized item(s) comprising: loading the 3D volume into a computer system; prioritizing item(s) within a 3D volume; utilization of prioritization of item(s) to determine which visualization augmentation strategy to implement to improve visualization; and, implement visualization augmentation strategy and display the augmented volume.

In some embodiments, a 3D volume comprises one of the group of a medical imaging volumetric dataset (e.g., CT, Mill, PET, SPECT, Ultrasound, Tomosynthesis, etc.) and non-medical volumetric datasets (e.g., video games that utilize 3D volumes, computer aided design, etc.).

In some embodiments, prioritizing item(s) includes the use of priority levels (e.g., a 10-point scale with 10 being the highest priority item(s) and 1 being the lowest priority item(s). In some embodiments, prioritizing item(s) based on item(s) property (e.g., contrast property, etc.). In some embodiments, prioritizing item(s) based on item(s) location (e.g., x,y,z location etc.). In some embodiments, prioritizing item(s) based on manual selection (e.g., arbitrary manual selection, random manual selection, human determined selection strategy, etc.). In some embodiments, prioritizing item(s) based on artificial intelligence (e.g., machine learning algorithm determines priority).

In some embodiments, an imaging finding comprises a zero-dimensional object or point. In some embodiments, an imaging finding comprises a one-dimensional object or line. In some embodiments, an imaging finding comprises a two-dimensional object (e.g., surface or pixel).

In some embodiments, an imaging finding comprises a three-dimensional object (e.g., voxels from CT or MRI scans, 3D object arranged from a collection of slices in computer aided design or video games, etc.). In some embodiments, an imaging finding comprises a N-dimensional object (e.g., voxel with multiple contrast-type parameters).

In some embodiments, visualization augmentation strategies of claim 1 include but are not limited to the following in the scenario wherein there are no non-prioritized items in between the viewing perspective(s) and the prioritized item(s): alter contrast property (e.g., change gray scale, change color, etc.) of the prioritized item(s) to improve visualization of the prioritized item(s); perform dynamic viewing (e.g., sequentially showing and hiding of a prioritized item such that it blinks to improve its visualization); and, performing voxel manipulation (e.g., increase size of voxel(s) comprising the prioritized item(s). An example would be wherein thickness information is needed (e.g., a dentist might be interested in the thickness of the enamel, but wants to know this information based on this patented prioritized volume rendered image). The contrast (e.g., color, grayscale) can be altered to signify the thickness of the enamel to satisfy the dentist's questions.

In some embodiments, visualization augmentation strategies of claim 1 include but are not limited to the following in the scenario wherein there are non-prioritized items in between the viewing perspectives and the prioritized item(s): complete preferential display of higher prioritized item(s) over lower prioritized items (i.e., any time that a non-prioritized item(s) is in between the viewing perspective(s) and prioritized item(s), the non-prioritized item is hidden); or, partial preferential display of higher prioritized item(s) over lower prioritized items (e.g., use dynamic filtration such that the prioritized item(s) are displayed for a greater fraction of time than the non-prioritized item(s)).

Some embodiments include implementing visualization augmentation strategy and display the augmented volume includes display on one of the group of 2D monitors (e.g., volume rendered images), augmented reality displays, mixed reality displays or virtual reality displays.

Some embodiments include implementing visualization augmentation strategy and display the augmented volume includes display on one of the group of 2D monitors (e.g., volume rendered images), augmented reality displays, mixed reality displays or virtual reality displays.

Some embodiments include utilization of multiple viewing perspectives, such that true 3D viewing with depth perception is accomplished. Some embodiments include utilization of alternative viewing angles. Some embodiments include utilization of convergence. Some embodiments include utilization of altering the interocular distance. Some embodiments include altering the field of view.

Based on this discussion, the terminology should no longer be titled "surface rendering image" because there would be holes in the surface (corresponding to the non-prioritized items) and display of the prioritized items that lie deeper. Furthermore, the terminology should also no longer be titled "volume rendering image" because certain items within the image are given higher priority and certain items within the image are given lower priority. In a standard volume rendering image, the voxels do not change based on the changing viewing perspective. In this patent's approach, the voxels are allocated priority levels. Furthermore, when the viewing perspectives change, the voxels that are rendered change (e.g., a low-priority voxel on the surface of a 3D volume may be displayed with one viewing perspective because there are no high-priority voxels behind it, but when the viewing perspective changes that same low-priority voxel on the surface of a 3D volume may be hidden because given the new viewing perspective a higher-priority voxel may now lie behind it). Based on this, when implementing a prioritization process and visualization augmentation strategy, such an image should be given the terminology "prioritized volume rendering".

In some embodiments, medical units of measure (e.g., Hounsfield) for a particular pixel(s)/voxel(s) may be of have a reading that could either be considered potentially dangerous or could also be benign. Under such a condition(s), the pixel(s)/voxel(s) would be assigned two unique priority levels. The properties associated with the pixel(s)/voxel(s) would be consistent with the display scheme selected by the user. During the review of the image set, the properties of the pixel(s)/voxel(s) could alternate every ('n' user selected) seconds. These properties would include but, not be limited to: color, contrast, grayscale, transparency.

In some embodiments, the user could select to perform statistical analysis on the entire data set of the pixels/voxels. For example, a useful analysis is to do a histogram of the medical units of measure (e.g., Hounsfield) of all of the pixels/voxels in the image set. The range of medical units for each particular bar would be specified by the user and/or by the medical facility involved. The histogram could be displayed before the user reviewed the image set. At that juncture, the user could assign the priority levels and properties associated with each level to the various bars in the histogram. Based on priority levels and properties associated with each level the pixels/voxels could be transformed for subsequent review by the user.

In further embodiments, for multiple image sets acquired over time, histograms with multiple bars could be presented for each set of tissue types. These histograms could be normalized to account for potential differences between image sets (e.g., the volume, number of images in the set, etc. might be different from one set to another). This process would facilitate comparisons over time to detect potential changes in a patient's condition.

In some embodiments, artificial intelligence (AI) could be employed in conjunction with priority levels for pixel(s)/voxel(s). The AI program could take into account multiple items which include but, are not limited to: the doctor's report when the patient entered the medical facility; laboratory results; current medication(s) list; reports from previous imaging sessions; prior hospitalizations; family doctor's reports; specialist visits reports, etc. The AI program taking these items into consideration could prepare a nominal draft priority level for different tissue types, body organ, region of the body of complaint, etc. If the draft priority levels were acceptable to the user, the properties associated with the priority levels could be ascribed to the pixels/voxels and the displayed images updated accordingly. This would help the user to focus on the highest priority areas.

In some embodiments, the artificial intelligence (AI), described above, could be used in conjunction with the statistical analysis, described above. The bars in the histogram could be in accordance with the properties selected by the user. The user could select to apply these properties and the display would adjust accordingly. For example, if the color red were assigned to tumorous tissue and high transparency were assigned to tissues of low priority levels, then the tumor would stand out. This method of application of AI coupled with statistical analysis could streamline the review process and accrue time savings.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A illustrates prior art viewing of a tumor growing at the right side of a vertebral body.

FIG. 1B illustrates current patent viewing of a tumor growing at the right side of a vertebral body.

FIG. 2A illustrates a first viewing perspective looking at a cluster of microcalcifications wherein some of the microcalcifications are determined to be benign and some of the microcalcifications are determined to be suspicious.

FIG. 2B illustrates an image of the cluster of microcalcifications from the viewing perspective in FIG. 2A wherein benign microcalcifications and suspicious microcalcifications are overlapped, which limits the ability to see the microcalcifications clearly.

FIG. 2C illustrates a prioritized volume rendering image of the cluster of microcalcifications from the viewing perspective in FIG. 2A wherein benign microcalcifications and suspicious microcalcifications are overlapped, but since prioritized volume rendering is performed, the suspicious microcalcifications are clearly seen.

FIG. 3A illustrates a second viewing perspective (the first viewing perspective was illustrated in FIG. 2A) looking at a cluster of microcalcifications wherein some of the microcalcifications are determined to be benign and some of the microcalcifications are determined to be suspicious.

FIG. 3B illustrates an image of the cluster of microcalcifications from the viewing perspective in FIG. 3A wherein benign microcalcifications and suspicious microcalcifications are overlapped, which limits the ability to see the microcalcifications clearly.

FIG. 3C illustrates a prioritized volume rendering image of the cluster of microcalcifications from the viewing perspective in FIG. 3A wherein benign microcalcifications and suspicious microcalcifications are overlapped, but since prioritized volume rendering is performed, the suspicious microcalcifications are clearly seen.

FIG. 16A illustrates a 10×10 matrix of data units of a contrast enhanced computed tomography (CT) scan of a carotid artery.

FIG. 16B illustrates prioritizing item(s) based on manual selection.

FIG. 18A illustrates which voxel of the three voxels is displayed based on a first Priority Level (PL) assignment.

FIG. 18B illustrates which voxel of the three voxels is displayed based on a second Priority Level (PL) assignment.

FIG. 18C illustrates which voxel of the three voxels is displayed based on a third Priority Level (PL) assignment.

FIG. 19A illustrates a first visual representation adjustment logic based on Priority Level.

FIG. 19B illustrates a second visual representation adjustment logic based on Priority Level.

FIG. 19C illustrates a third visual representation adjustment logic based on Priority Level.

FIG. 20A illustrates a 10×10 matrix of data units of a contrast enhanced computed tomography (CT) scan of a carotid artery.

FIG. 20B illustrates prioritizing item(s) based on item(s) property (e.g., contrast property, etc.).

FIG. 21A illustrates a 10×10 matrix of data units of a contrast enhanced computed tomography (CT) scan of a carotid artery.

FIG. 21B illustrates prioritizing item(s) based on item(s) location (e.g., x,y,z location etc.).

FIG. 22A illustrates a 10×10 matrix of data units of a contrast enhanced computed tomography (CT) scan of a carotid artery.

FIG. 22B illustrates prioritizing item(s) based on manual selection.

FIG. 23A illustrates a 10×10 matrix of data units of a contrast enhanced computed tomography (CT) scan of a carotid artery.

FIG. 23B illustrates prioritizing item(s) based on artificial intelligence (e.g., machine learning algorithm determines priority).

FIG. 34A illustrates an axial CT scan of a thoracic vertebral and left eye and right eye view points and left and right eye viewing angles for depth 3-dimensional viewing.

FIG. 34B illustrates an extended reality headset.

FIG. 34C illustrates an axial CT scan of a thoracic vertebral and left eye and right eye view points and left and right eye viewing angles for depth 3-dimensional viewing with portions of the image marked up to illustrate prioritized volume rendering.

FIG. 34D illustrates an extended reality headset with images acquired through prioritized volume rendering, which overcomes the limitation a deeper structure being hidden by superficial structures.

DETAILED DESCRIPTIONS

Figure 4:
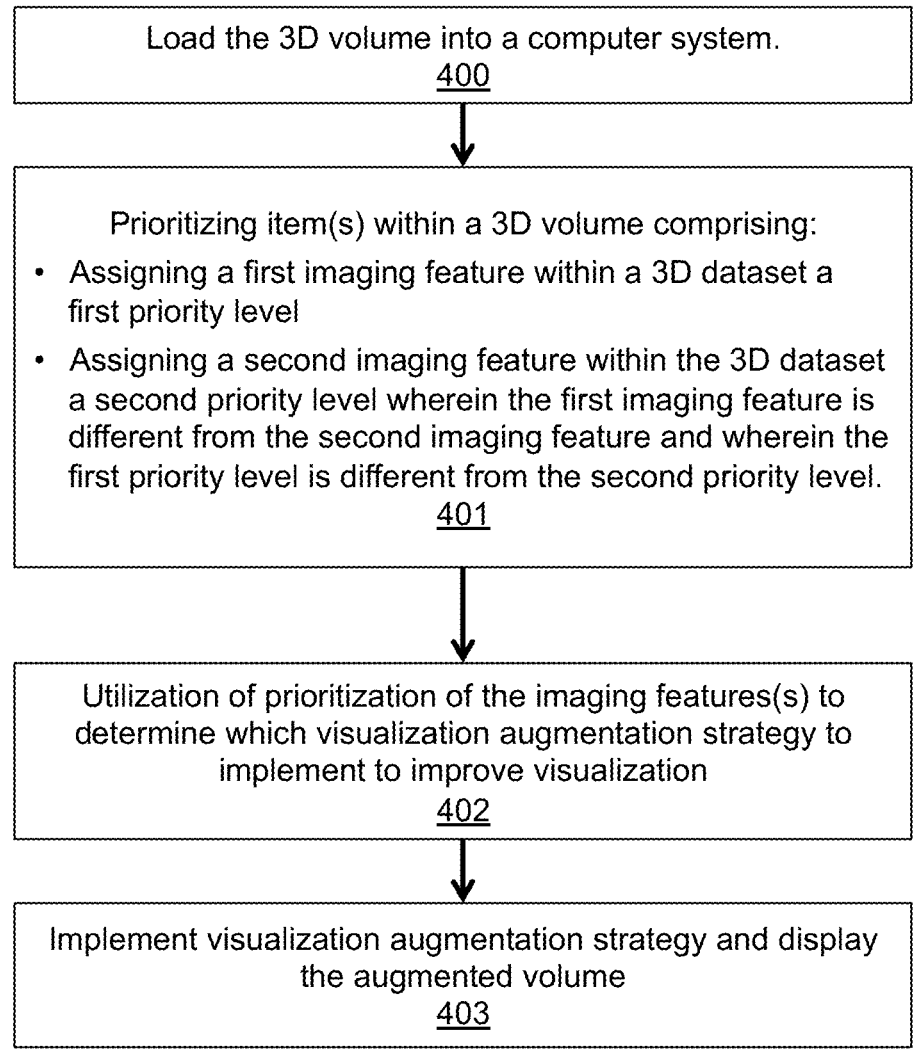
FIG. 4 illustrates a flow diagram showing the method of augmenting visualization of item(s) within a 3D volume to improve visualization of prioritized item(s).

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

FIG. 1A illustrates prior art viewing of a tumor growing at the right side of a vertebral body. 100 illustrates a vertebral body as shown from the anterior (front) perspective. Assume the vertebral body has Hounsfield Units of 300. 101 illustrates a tumor growing at the right side of the vertebral body. Assume the tumor has Hounsfield Units of 50. 102 illustrates a viewing perspective from the right side. 103 illustrates a viewing perspective from the left side. 104 illustrates a monitor showing the view from the viewing perspective from the right side 102. Note that this viewing angle shows both the right side of the vertebral body 100 and the tumor 101. 105 illustrates a monitor showing the view from the viewing perspective from the left side 103. Note that this viewing angle shows only the left side of the vertebral body. This illustrates that a volume rendered image can show a finding of interest (e.g., a tumor) from a first angle and also shows that a finding of interest can be hidden from a second angle.

FIG. 1B illustrates current patent viewing of a tumor growing at the right side of a vertebral body. 100 illustrates a vertebral body as shown from the anterior (front) perspective. Assume the vertebral body has Hounsfield Units of 300. Note that the priority level assigned is 3. 101 illustrates a tumor growing at the right side of the vertebral body. Assume the tumor has Hounsfield Units of 50. Note that the priority level assigned is 10. 102 illustrates a viewing perspective from the right side. 103 illustrates a viewing perspective from the left side. 106 illustrates a monitor showing the view from the viewing perspective from the right side 102. Note that this viewing angle shows both the right side of the vertebral body 100 and the tumor 101. 107 illustrates a monitor showing the view from the viewing perspective from the left side 103. Note that this viewing angle shows both the left side of the vertebral body 100 and the tumor 101. This illustrates that using prioritized volume rendering, a finding of interest (e.g., a tumor) can be seen from all angles. This improves upon the prior art of conventional volume rendering because this process of prioritized volume rendering allows a dangerous finding (e.g., tumor) to be seen from all angles. It also retains the ability to see other adjacent structures, which allows the user to have context. Additionally, please note that it is anticipated that the additional techniques as disclosed in U.S. patent application Ser. No. 16/785,606 which is incorporated by reference, Improving image processing via a modified segmented structure, can be coupled together with techniques disclosed this patent to improve visualization of small prioritized lesions.

FIG. 2A illustrates a first viewing perspective looking at a cluster of microcalcifications wherein some of the microcalcifications are determined to be benign and some of the microcalcifications are determined to be suspicious. 200 illustrates a cluster of 16 microcalcifications, of which 3 are determined (by an artificial intelligence algorithm) to be suspicious and 13 are determined (by an artificial intelligence algorithm) to be benign. 201 illustrates a viewing perspective. 202 illustrates a first suspicious microcalcification. Note that from the viewing perspective 201, the first suspicious microcalcification 202 will be partially hidden by a first benign microcalcification 203, a second benign microcalcification 204 and a third benign microcalcification 205. 206 illustrates a second suspicious microcalcification. Note that from the viewing perspective 201, the second suspicious microcalcification 206 is partially obscured by a fourth benign microcalcification 207 and a fifth benign microcalcification 208. 209 illustrates a third suspicious microcalcification. Note that from the viewing perspective 201, the third suspicious microcalcification 209 is partially obscured by a sixth benign microcalcification 210 and also note that there is a seventh benign microcalcification 211 located behind it, which could also impair visualization of the third suspicious microcalcification 209. Note that 212 represents an eighth benign microcalcification, which is not overlapping with any of the suspicious microcalcifications from viewing perspective 201. Note that 213 represents an ninth benign microcalcification, which is not overlapping with any of the suspicious microcalcifications from viewing perspective 201. Note that 214 represents an tenth benign microcalcification, which is not overlapping with any of the suspicious microcalcifications from viewing perspective 201. Note that 215 represents an eleventh benign microcalcification, which is not overlapping with any of the suspicious microcalcifications from viewing perspective 201. Note that 216 represents an twelfth benign microcalcification, which is not overlapping with any of the suspicious microcalcifications from viewing perspective 201. Note that 217 represents an thirteenth benign microcalcification, which is not overlapping with any of the suspicious microcalcifications from viewing perspective 201.

FIG. 2B illustrates a conventional volume rendering image of the cluster of microcalcifications from the viewing perspective in FIG. 2A wherein benign microcalcifications and suspicious microcalcifications are overlapped, which limits the ability to see the microcalcifications clearly. 200 illustrates a cluster of 16 microcalcifications, of which 3 are determined (by an artificial intelligence algorithm) to be suspicious and 13 are determined (by an artificial intelligence algorithm) to be benign. 201 illustrates a viewing perspective. 202 illustrates a first suspicious microcalcification. Note that from the viewing perspective 201, the first suspicious microcalcification 202 will be partially hidden by a first benign microcalcification 203, a second benign microcalcification 204 and a third benign microcalcification 205. 206 illustrates a second suspicious microcalcification. Note that from the viewing perspective 201, the second suspicious microcalcification 206 is partially obscured by a fourth benign microcalcification 207 and a fifth benign microcalcification 208. 209 illustrates a third suspicious microcalcification. Note that from the viewing perspective 201, the third suspicious microcalcification 209 is partially obscured by a sixth benign microcalcification 210 and also note that there is a seventh benign microcalcification 211 located behind it, which could also impair visualization of the third suspicious microcalcification 209. Note that 212 represents an eighth benign microcalcification, which is not overlapping with any of the suspicious microcalcifications from viewing perspective 201. Note that 213 represents an ninth benign microcalcification, which is not overlapping with any of the suspicious microcalcifications from viewing perspective 201. Note that 214 represents an tenth benign microcalcification, which is not overlapping with any of the suspicious microcalcifications from viewing perspective 201.

Note that 215 represents an eleventh benign microcalcification, which is not overlapping with any of the suspicious microcalcifications from viewing perspective 201. Note that 216 represents an twelfth benign microcalcification, which is not overlapping with any of the suspicious microcalcifications from viewing perspective 201. Note that 217 represents an thirteenth benign microcalcification, which is not overlapping with any of the suspicious microcalcifications from viewing perspective 201. Therefore, a volume rendering image from viewing perspective 201 will yield a limited assessment of the three suspicious microcalcifications 202, 206 and 211, as shown on monitor 218.

FIG. 2C illustrates a prioritized volume rendering image of the cluster of microcalcifications from the viewing perspective in FIG. 2A wherein benign microcalcifications and suspicious microcalcifications are overlapped. This figure illustrates how utilization of a prioritized volume rendering process can improve visualization of the suspicious microcalcifications, which are assigned high priority levels. 200 illustrates a cluster of 9 microcalcifications, of which 3 are determined (by an artificial intelligence algorithm) to be suspicious and 6 are determined (by an artificial intelligence algorithm) to be benign. Note that 7 of the benign microcalcifications were in the way from visualization of the suspicious microcalcifications and were therefore not rendered while viewing from viewing perspective 201, which is in accordance with an embodiment of the prioritized volume rendering process. 202 illustrates a first suspicious microcalcification. Note that from the viewing perspective 201 in FIG. 2A, the first suspicious microcalcification 202 would have been partially hidden by a first benign microcalcification 203, a second benign microcalcification 204 and a third benign microcalcification 205. Since the suspicious microcalcification 202 has a higher priority (e.g., priority level 10) and the benign microcalcifications have a lower priority (e.g., priority level 5), the benign microcalcifications are not rendered in this prioritized volume rendering process during this specific viewing angle as shown in the monitor 213. 206 illustrates a second suspicious microcalcification. Note that from the viewing perspective 201 in FIG. 2A, the second suspicious microcalcification 206 is partially obscured by a fourth benign microcalcification 207 and a fifth benign microcalcification 208. Since the suspicious microcalcification 206 has a higher priority (e.g., priority level 10) and the benign microcalcifications have a lower priority (e.g., priority level 5), the benign microcalcifications are not rendered in this prioritized volume rendering process during this specific viewing angle as shown in the monitor 213. 209 illustrates a third suspicious microcalcification. Note that from the viewing perspective 201 in FIG. 2A, the third suspicious microcalcification 209 is partially obscured by a sixth benign microcalcification 210 and also note that there is a seventh benign microcalcification 211 located behind it, which could also impair visualization of the third suspicious microcalcification 209. Since the suspicious microcalcification 209 has a higher priority (e.g., priority level 10) and the benign microcalcifications have a lower priority (e.g., priority level 5), the benign microcalcifications are not rendered in this prioritized volume rendering process during this specific viewing angle as shown in the monitor 219. Note that 212 represents an eighth benign microcalcification, which is not overlapping with any of the suspicious microcalcifications from viewing perspective 201 is rendered. Note that 213 represents an ninth benign microcalcification, which is not overlapping with any of the suspicious microcalcifications from viewing perspective 201 is rendered. Note that 214 represents an tenth benign microcalcification, which is not overlapping with any of the suspicious microcalcifications from viewing perspective 201 is rendered. Note that 215 represents an eleventh benign microcalcification, which is not overlapping with any of the suspicious microcalcifications from viewing perspective 201 is rendered.

Note that 216 represents an twelfth benign microcalcification, which is not overlapping with any of the suspicious microcalcifications from viewing perspective 201 is rendered. Note that 217 represents an thirteenth benign microcalcification, which is not overlapping with any of the suspicious microcalcifications from viewing perspective 201 is rendered. Therefore, a prioritized volume rendering image from viewing perspective 201 will yield an improved visualization of the three suspicious microcalcifications 202, 206 and 211. Note that prioritized volume rendering provides an optimized view of the structures of interest no matter what the viewing angle.

FIG. 3A illustrates a first viewing perspective looking at a cluster of microcalcifications wherein some of the microcalcifications are determined to be benign and some of the microcalcifications are determined to be suspicious. 200 illustrates a cluster of 16 microcalcifications, of which 3 are determined (by an artificial intelligence algorithm) to be suspicious and 13 are determined (by an artificial intelligence algorithm) to be benign. Note that 200 is the same cluster of microcalcifications as shown in FIG. 2A. 301 illustrates a second viewing perspective (note that the viewing perspective shown here in 301 is different from the viewing perspective 201 shown in FIG. 2A). 202 illustrates the first suspicious microcalcification. Note that 212 represents an eighth benign microcalcification, which is potentially overlapping with the first suspicious microcalcification 202 from viewing perspective 301. Note that 214 represents an tenth benign microcalcification, which is potentially overlapping with the first suspicious microcalcification 202 from viewing perspective 301. Note that 215 represents an eleventh benign microcalcification, which is potentially overlapping with the first suspicious microcalcification 202 from viewing perspective 301. 206 illustrates the second suspicious microcalcification. Note that 204 represents the second benign microcalcification, which is overlapping with the second suspicious microcalcification 206 from viewing perspective 301. Note that 210 represents an sixth benign microcalcification, which is overlapping with the second suspicious microcalcification 206 from viewing perspective 301. Note that 216 represents an twelfth benign microcalcification, which is overlapping with the second suspicious microcalcification 206 from viewing perspective 301. 209 illustrates the third suspicious microcalcification. Note that 203 represents the first benign microcalcification, which is not overlapping with the third suspicious microcalcification 209 from viewing perspective 301. Note that 205 represents an third benign microcalcification, which is not overlapping with any of the suspicious microcalcifications from viewing perspective 301. Note that 207 represents an fourth benign microcalcification, which is not overlapping with any of the suspicious microcalcifications from viewing perspective 301. Note that 208 represents an fifth benign microcalcification, which is not overlapping with any of the suspicious microcalcifications from viewing perspective 301. Note that 211 represents an seventh benign microcalcification, which is not overlapping with any of the suspicious microcalcifications from viewing perspective 301. Note that 213 represents an ninth benign microcalcification, which is not overlapping with any of the suspicious microcalcifications from viewing perspective 301. Note that 217 represents an thirteenth benign microcalcification, which is not overlapping with any of the suspicious microcalcifications from viewing perspective 301.

FIG. 3B illustrates an image of the cluster of microcalcifications from the viewing perspective in FIG. 2A wherein benign microcalcifications and suspicious microcalcifications are overlapped, which limits the ability to see the microcalcifications clearly. 200 illustrates a cluster of 16 microcalcifications, of which 3 are determined (by an artificial intelligence algorithm) to be suspicious and 13 are determined (by an artificial intelligence algorithm) to be benign. Note that 200 is the same cluster of microcalcifications as shown in FIG. 2A. 301 illustrates a second viewing perspective (note that the viewing perspective shown here in 301 is different from the viewing perspective 201 shown in FIG. 2A). 202 illustrates the first suspicious microcalcification. Note that 212 represents an eighth benign microcalcification, which is potentially overlapping with the first suspicious microcalcification 202 from viewing perspective 301. Note that 214 represents an tenth benign microcalcification, which is potentially overlapping with the first suspicious microcalcification 202 from viewing perspective 301. Note that 215 represents an eleventh benign microcalcification, which is potentially overlapping with the first suspicious microcalcification 202 from viewing perspective 301. 206 illustrates the second suspicious microcalcification. Note that 204 represents the second benign microcalcification, which is overlapping with the second suspicious microcalcification 206 from viewing perspective 301. Note that 210 represents an sixth benign microcalcification, which is overlapping with the second suspicious microcalcification 206 from viewing perspective 301. Note that 216 represents an twelfth benign microcalcification, which is overlapping with the second suspicious microcalcification 206 from viewing perspective 301. 209 illustrates the third suspicious microcalcification. Note that 203 represents the first benign microcalcification, which is overlapping with the third suspicious microcalcification 209 from viewing perspective 301. Note that 205 represents an third benign microcalcification, which is not overlapping with any of the suspicious microcalcifications from viewing perspective 301. Note that 207 represents an fourth benign microcalcification, which is not overlapping with any of the suspicious microcalcifications from viewing perspective 301. Note that 208 represents an fifth benign microcalcification, which is not overlapping with any of the suspicious microcalcifications from viewing perspective 301. Note that 211 represents an seventh benign microcalcification, which is not overlapping with any of the suspicious microcalcifications from viewing perspective 301. Note that 213 represents an ninth benign microcalcification, which is not overlapping with any of the suspicious microcalcifications from viewing perspective 301. Note that 217 represents an thirteenth benign microcalcification, which is not overlapping with any of the suspicious microcalcifications from viewing perspective 301.

FIG. 3C illustrates an image of the cluster of microcalcifications from the viewing perspective in FIG. 2A wherein benign microcalcifications and suspicious microcalcifications are overlapped, which limits the ability to see the microcalcifications clearly. 200 illustrates a cluster of 16 microcalcifications, of which 3 are determined (by an artificial intelligence algorithm) to be suspicious and 13 are determined (by an artificial intelligence algorithm) to be benign. Note that 200 is the same cluster of microcalcifications as shown in FIG. 2A. 202 illustrates the first suspicious microcalcification. Note that the eighth benign microcalcification 212, the tenth benign microcalcification 214 and the eleventh benign microcalcification which were overlapping from viewing perspective 301 are not rendered in accordance with the prioritized volume rendering process, which improves visualization of the first suspicious microcalcification 202. 206 illustrates the second suspicious microcalcification. Note that the second benign microcalcification 204, the sixth benign microcalcification 210 and the twelfth benign microcalcification 216 which were overlapping from viewing perspective 301 are not rendered in accordance with the prioritized volume rendering process, which improves visualization of the second suspicious microcalcification 205. 209 illustrates the third suspicious microcalcification. Note that the third benign microcalcification. Note that the first benign microcalcification 203, which was overlapping with the third suspicious microcalcification 209 from viewing perspective 301 is not rendered in accordance with the prioritized volume rendering process, which improves visualization of the second suspicious microcalcification 205. Note that 205 represents an third benign microcalcification, which is not overlapping with any of the suspicious microcalcifications from viewing perspective 301 is rendered. Note that 207 represents an fourth benign microcalcification, which is not overlapping with any of the suspicious microcalcifications from viewing perspective 301 is rendered. Note that 208 represents an fifth benign microcalcification, which is not overlapping with any of the suspicious microcalcifications from viewing perspective 301 is rendered. Note that 211 represents an seventh benign microcalcification, which is not overlapping with any of the suspicious microcalcifications from viewing perspective 301 is rendered. Note that 213 represents an ninth benign microcalcification, which is not overlapping with any of the suspicious microcalcifications from viewing perspective 301 is rendered. Note that 217 represents an thirteenth benign microcalcification, which is not overlapping with any of the suspicious microcalcifications from viewing perspective 301 is rendered. Therefore, a prioritized volume rendering image from viewing perspective 301 will yield an improved visualization of the three suspicious microcalcifications 202, 206 and 211. Note that prioritized volume rendering provides an optimized view of the structures of interest no matter what the viewing angle.

FIG. 4 illustrates a flow diagram showing the method of augmenting visualization of item(s) within a 3D volume to improve visualization of prioritized item(s). This method comprises loading the 3D volume into a computer system 400; prioritizing item(s) within a 3D volume comprising assigning a first imaging feature within a 3D dataset a first priority level; and assigning a second imaging feature within the 3D dataset a second priority level wherein the first imaging feature is different from the second imaging feature and wherein the first priority level is different from the second priority level; 401; utilization of prioritization of item(s) to determine which visualization augmentation strategy to implement to improve visualization 402; implement visualization augmentation strategy and display the augmented volume 403.

Figure 5:
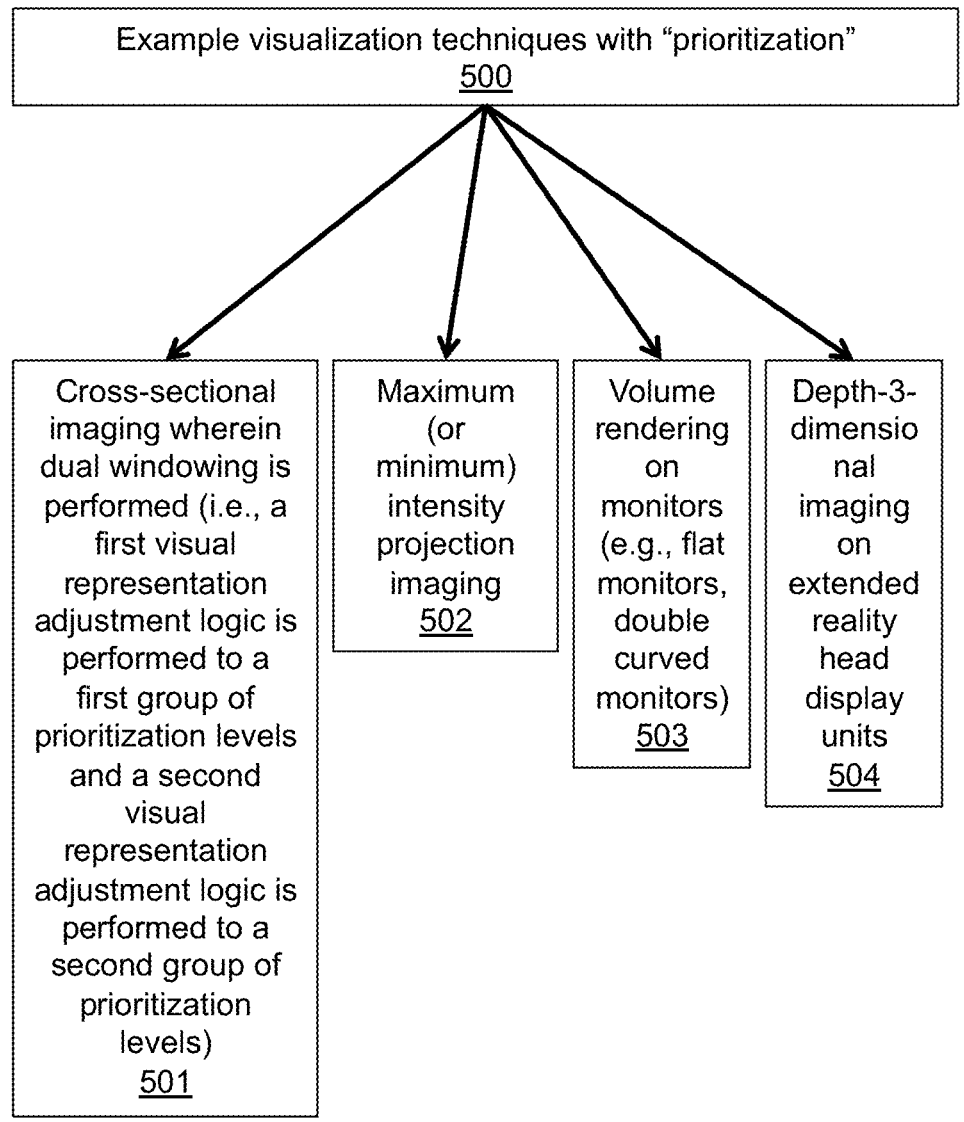
FIG. 5 illustrates example visualization techniques with "prioritization".

FIG. 5 illustrates example visualization techniques with "prioritization". 500 illustrates example visualization techniques with "prioritization". 501 illustrates cross-sectional imaging wherein dual windowing is performed (i.e., a first visual representation adjustment logic is performed to a first group of prioritization levels and a second visual representation adjustment logic is performed to a second group of prioritization levels). For example, assume that an artificial intelligence algorithm reviews a CT scan of the abdomen and determines that there is a pancreatic tumor and marks the voxels pertaining to the suspected pancreatic tumor as high priority voxels. Next, assume that the suspected lesion wants to be better visualized using a combination of double windowing as described in U.S. Pat. No. 10,586,400 and halo visualization techniques described in U.S. patent application Ser. No. 16/785,606. The prioritization scheme can be utilized in combination with these techniques to highlight (e.g., use false color) for the area of concern and make other voxels in the dataset subdued. In 502, the prioritization can be used with maximum intensity projection (MIP) or minimum intensity projection (MinIP) type imaging. For example, the most dangerous findings may not correspond to the findings with the highest Hounsfield Units. Therefore, it is important to bring out, through the prioritization techniques disclosed in this patent, imaging features deemed to be important on such MIP or MinIP images. In 503, the volume rendering on monitors can be performed on computer or television screens. Examples include, but are not limited to, the following: flat 2D monitors; curved monitors; and, double curved monitors. In 504, the depth-3-dimensional imaging on extended reality head display units can also utilize prioritized volume rendering in its display.

Figure 6:
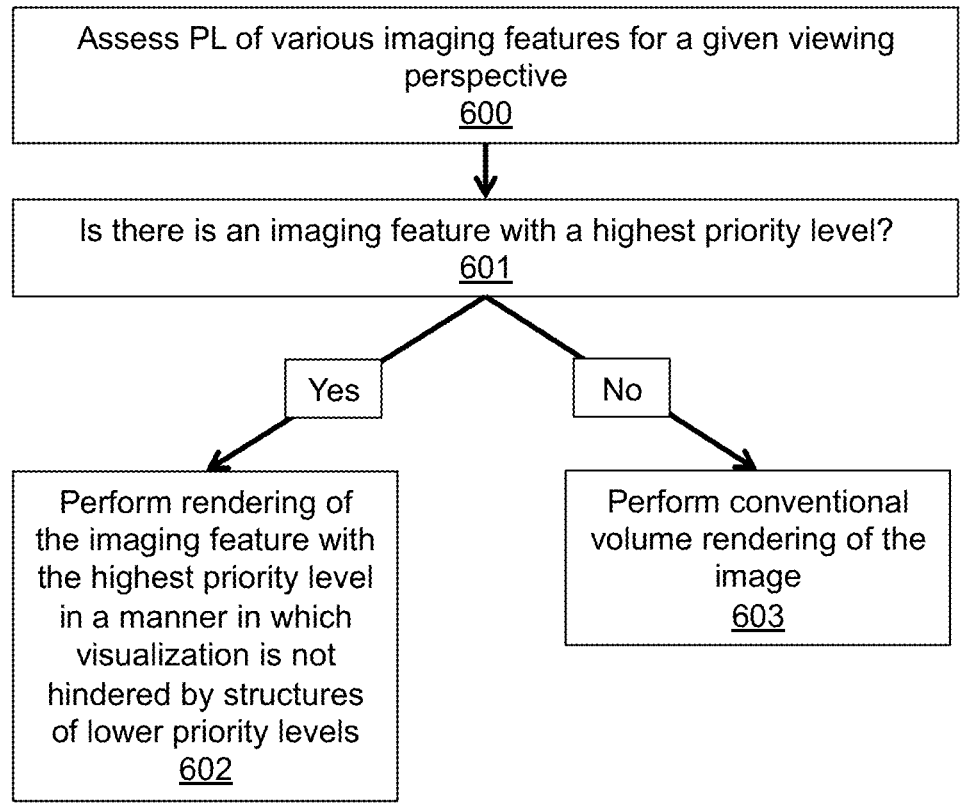
FIG. 6 illustrates the process for performing prioritized volume rendering.

FIG. 6 illustrates the process for performing prioritized volume rendering. Processing block 600 illustrates assessing the priority level (PL) of various imaging features for a given viewing perspective. Processing block 601 illustrates determining "is there is an imaging feature with a highest priority level?" In other words, the question of "do all imaging features from the given perspective have the same priority level or are they different?" needs to be answered. If there are imaging features with different priority levels, then proceed to processing block 102. Processing block 602 is to perform rendering of the imaging feature with the highest priority level in a manner in which visualization is not hindered by structures of lower priority levels. If all imaging features have the same priority level, then proceed to processing block 603. Processing block 603 is to perform conventional volume rendering of the image. Note that in practice, the entirety of the field of view will not likely be filled with prioritized imaging features, therefore this approach achieves the important goal of optimally displaying prioritized structures while also including additional non-prioritized imaging features for context.

Figure 7:
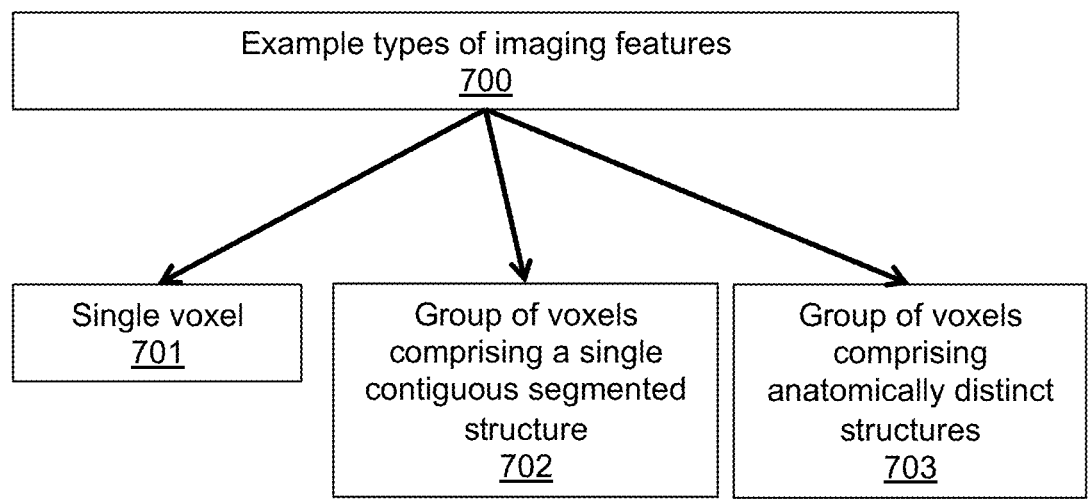
FIG. 7 illustrates a range of imaging features that can be grouped together for assignment of a priority level.

FIG. 7 illustrates a range of imaging features that can be grouped together for assignment of a priority level. 700 illustrates types of imaging features. Most imaging findings pertinent to a radiologist comprise a cluster of adjacent voxels. For example, even a small pulmonary nodule of 3 mm in size comprises several voxels on modern CT imaging examinations. That being said, there is some examples wherein an imaging feature can be used as a single voxel, as indicated by 701. For example, some anatomic landmarks, such as reference points could be used. 702 illustrates a group of voxels comprising a single contiguous segmented structure. An example of this would be a pulmonary nodule. 703 illustrates a group of voxels comprising a group of voxels of anatomically distinct structures.

Figure 8:
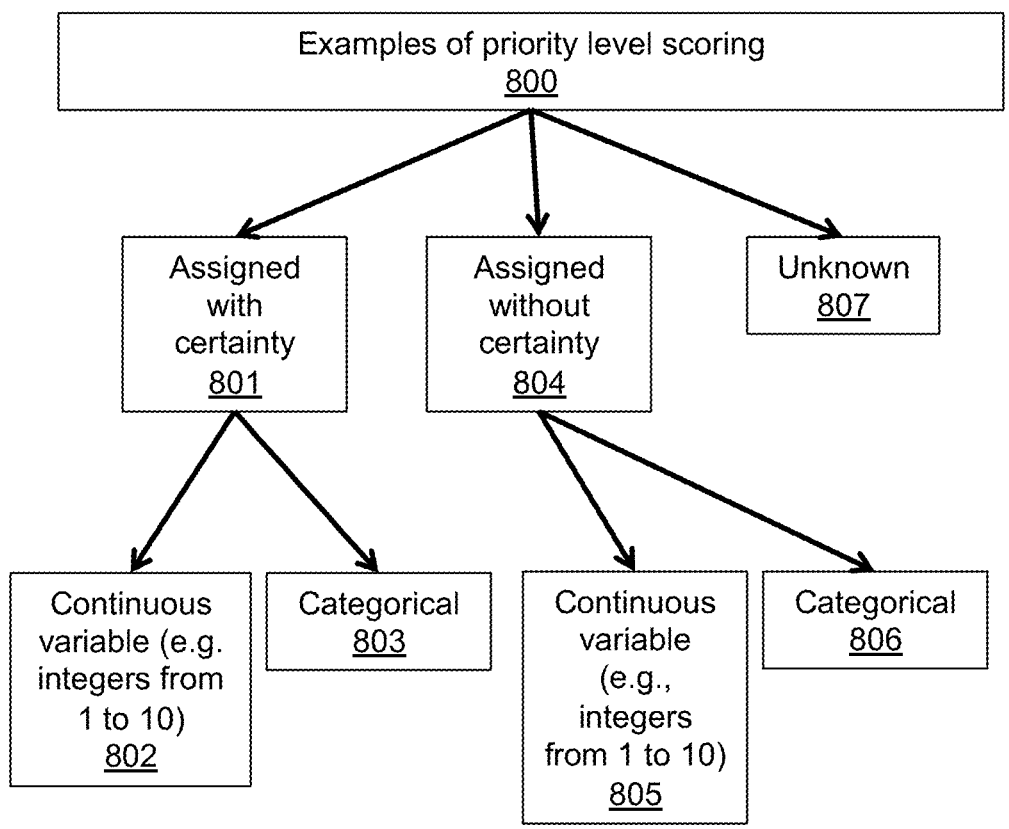
FIG. 8 illustrates examples of priority level scoring.

FIG. 8 illustrates examples of priority level scoring. 800 illustrates examples of priority level scoring. 801 illustrates a category wherein imaging features are assigned with high level of certainty. For example, an imaging feature can be classified as "high level of certainty" if it there is data in categories "A", "B", and "C". Among the category wherein imaging features are assigned with a high level of certainty 801, example coding of the variables includes continuous variables 802 and categorical variables 803. Throughout this patent, the most common type of priority level coded used is integers ranging between 1 and 10. If there is missing data (e.g., an imaging feature has data only in category "C"), then the imaging feature can be classified as assigned without certainty 804. Among the category wherein imaging features are assigned without certainty 804, example coding of the variables includes continuous variables 805 and categorical variables 806. Throughout this patent, the most common type of priority level coded used is integers ranging between 1 and 10. Also, please note that the preferred method to communicate the certainty level is through altered visual representation adjustment logic, such as is used by U.S. Pat. No. 10,586,400, which is incorporated by reference. Also, methods disclosed in WO2019195022A1 can also be implemented to denote certainty levels to a user, which is incorporated by reference. Finally, 807 denotes a category wherein priority level is unknown.

Figure 9:
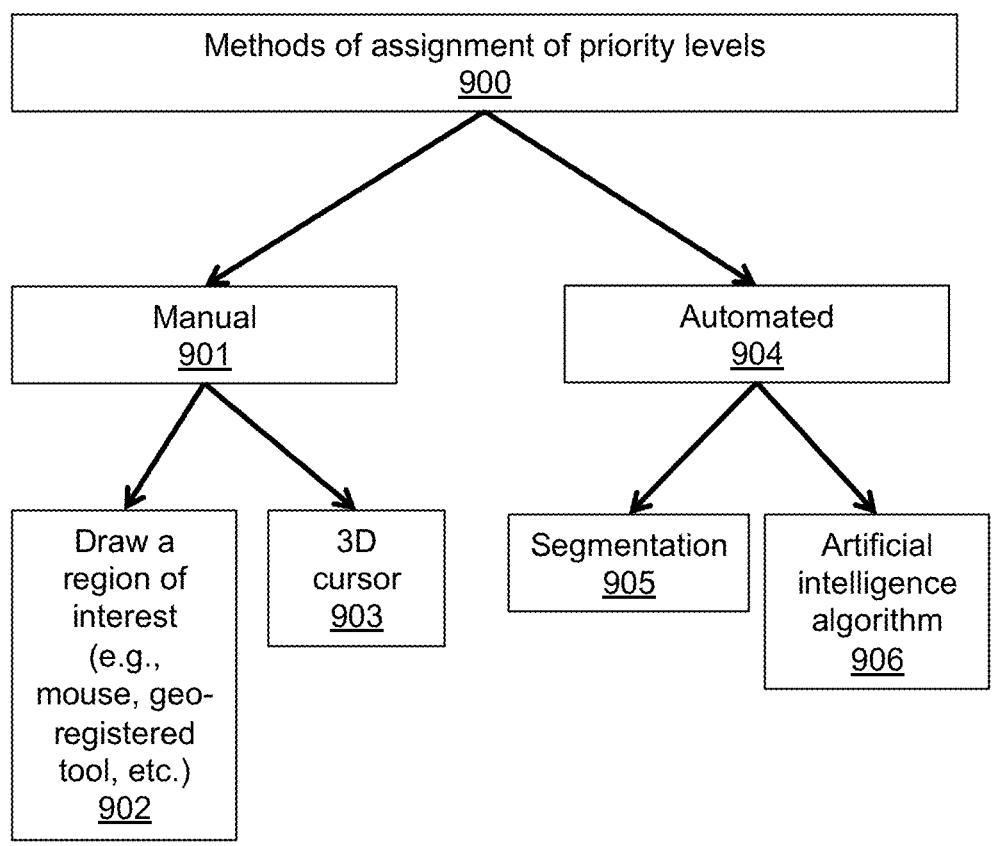
FIG. 9 illustrates methods of assigning priority levels.

FIG. 9 illustrates methods of assigning priority levels. 900 illustrates assigning priority levels to an image. 901 illustrates the first example type, which is through manual assignment. 902 illustrates the manual method wherein a user draws a region of interest over a portion of the image. A first example method could be through pointing and clicking with a mouse to select a portion of the image. For example, a user could click, then move the mouse in a motion such that the mouse cursor circles the particular imaging feature and then click again. The imaging feature is then selected. Alternatively, the imaging feature could be selected using a virtual tool, such as techniques as described in PCT/US19/47891, which is incorporated by reference. Alternatively, the user could perform techniques disclosed in U.S. patent application Ser. No. 16/524,275, which is incorporated by reference. Additionally, the manual assignment of priority levels could be accomplished through inputs through the 3D cursor 903, such as described in U.S. Pat. No. 9,980,691, which is incorporated by reference. In addition to manual assignment methods, assignment could be performed through automated methods 904. A first automated method for assigning priority levels to an imaging feature is through segmentation 905. Some segmentation methods currently exist, such as using the Montreal Neuroimaging Atlas for segmenting the brain. The segmented structure can be assigned a priority level based on an automated process. For example, the pituitary gland is automatically assigned a priority level of an 8 because it is deemed an important structure at baseline. Such automated methods can be enhanced by utilizing patient inputted histories, such as if the history "hypogonadism" was provided, the pituitary gland would automatically be assigned a 10 for the priority level. Thus, patient history can factor in to the priority level assignment, which can be done through segmentation on an automated fashion. Additionally, artificial intelligence algorithms can assign priority levels to imaging features within the 3D imaging dataset. This is useful because the artificial intelligence algorithms 906 can help the user visualize the most important imaging features therefore spent the most time on what counts the most. Additional factors that can be utilized in conjunction with the manual assignment 901 techniques or the automated techniques 904 include assignment based on: contrast property (e.g., Hounsfield unit); location of the imaging features; level of dangerous level of an imaging feature, such as is disclosed in U.S. patent application Ser. No. 16/597,910, which is incorporated by reference; the probability of an imaging feature harboring pathology; and, the checklist item of a radiologist.

Figure 10:
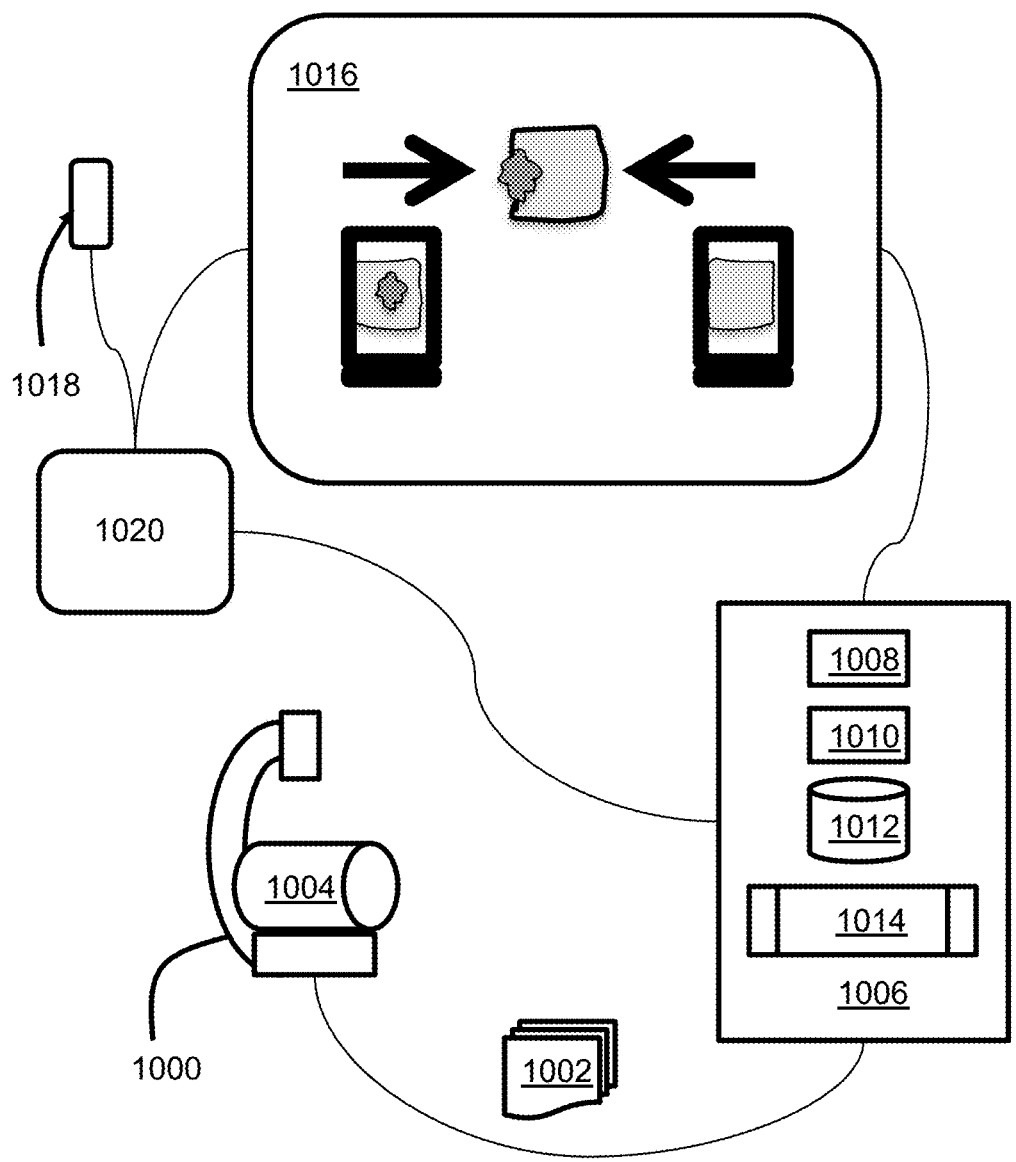
FIG. 10 illustrates an overview of the apparatus used for the assignment of priority levels into a 3D imaging dataset.

FIG. 10 illustrates an overview of the apparatus used for the assignment of priority levels into a 3D imaging dataset. A radiologic imaging system 1000 (e.g., X-ray, ultrasound, CT (computed Tomography), PET (Positron Emission Tomography), or MRI (Magnetic Resonance Imaging)) is used to generate 2D medical images 1002 of an anatomic structure 904 of interest. The 2D medical images 1002 are provided to an image processor 1006, that includes processors 1008 (e.g., CPUs and GPUs), volatile memory 1010 (e.g., RAM), and non-volatile storage 1012 (e.g. HDDs and SSDs). A program 1014 running on the image processor implements one or more of the steps described in FIG. 1. 3D medical images are generated from the 2D medical images and displayed on an TO device 1016. The TO device may include a virtual or augmented reality headset, monitor, tablet computer, PDA (personal digital assistant), mobile phone, or any of a wide variety of devices, either alone or in combination. The TO device may include a touchscreen and, may accept input from external devices (represented by 1018) such as a keyboard, mouse, and any of a wide variety of equipment for receiving various inputs. However, some or all the inputs could be automated, e.g. by the program 1014. Finally, as discussed further in this patent, a series of virtual tools 1020 are implemented, which facilitate viewing of medical images by person(s) playing the game(s).

Figure 11:
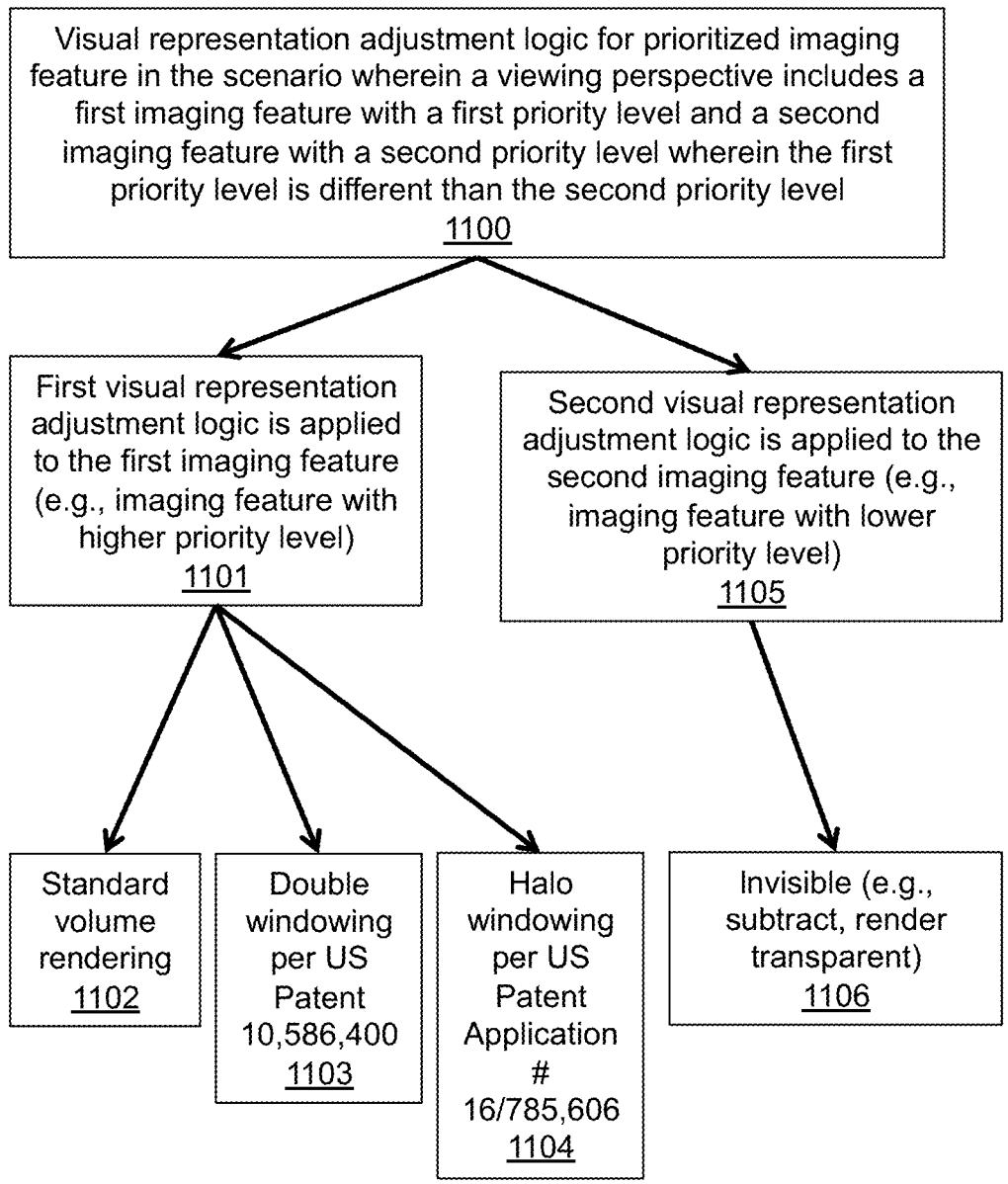
FIG. 11 illustrates examples of visual representation adjustment logic that can be used in conjunction with priority levels, so as to improve visualization of the imaging feature with the higher assigned priority level.

FIG. 11 illustrates examples of visual representation adjustment logic that can be used in conjunction with priority levels, so as to improve visualization of the imaging feature with the higher assigned priority level. 1100 illustrates wherein visual representation adjustment logic for prioritized imaging feature in the scenario wherein a viewing perspective includes a first imaging feature with a first priority level and a second imaging feature with a second priority level wherein the first priority level is different than the second priority level. A first visual representation adjustment logic is applied to the first imaging feature (e.g., imaging feature with higher priority level) as illustrated in 1101. For example, standard volume rendering techniques can be performed wherein a threshold is used (e.g., to select the bones, but subtract other structures), as illustrated in 1102. Additionally, as illustrated in 1103, double windowing techniques could be performed in accordance with U.S. Pat. No. 10,586,400 so as to improve visualization of the imaging feature(s) with the higher priority level. Additionally, as illustrated in 1104, to improve visualization of the structure of interest, some portions of the image can be deliberately made more emphasized and other portions made more subdued, as is disclosed in Ser. No. 16/785,606. A second visual representation adjustment logic is applied to the second imaging feature (e.g., imaging feature with lower priority level) as illustrated in 1105. Note that the first visual representation adjustment logic is different from the second visual representation adjustment logic. Also note that the first imaging feature is different from the second imaging feature. The preferred embodiment for the visual representation adjustment logic for the second imaging feature is to render it invisible, as shown in 1106.

Figure 12:
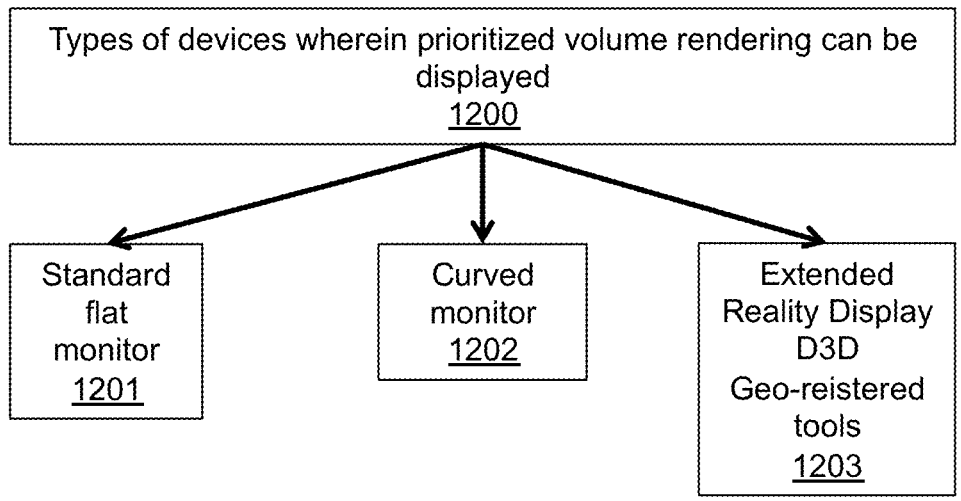
FIG. 12 illustrates various types of devices wherein prioritized volume rendering can be displayed.

FIG. 12 illustrates various types of devices wherein prioritized volume rendering can be displayed. 1200 illustrates types of devices wherein prioritized volume rendering can be displayed. 1201 illustrates a standard flat screen monitor. 1202 illustrates a curved monitor. 1203 illustrates an extended reality head display unit.

Figure 13A:
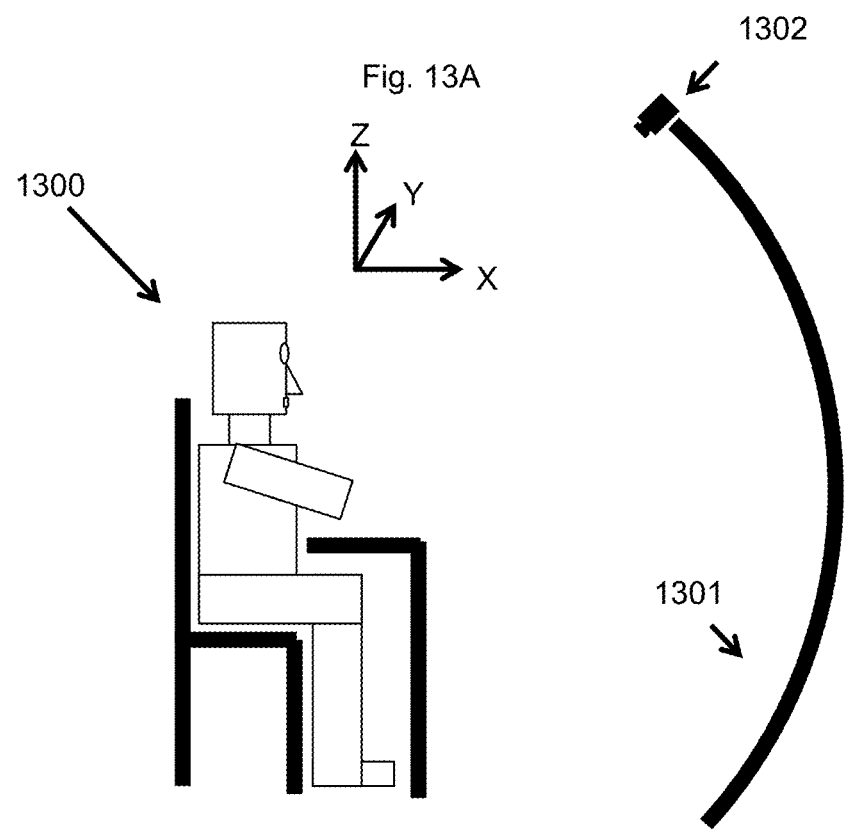
FIG. 13A illustrates a side view of a screen upon which a user could view a prioritized volume rendered image.

FIG. 13A illustrates a side view of a screen upon which a user could view a prioritized volume rendered image. 1300 illustrates a radiologist sitting at a desk. 1301 illustrates a curved screen, which is curved in the x-z plane. 1302 illustrates an eye tracking camera. The eye tracking camera is useful because it can track where the user is looking on the screen, which can then alter the appearance of the image as described in 62/985,363. In some embodiments, however, the eye tracking can serve as an input for prioritizing an imaging feature.

Figure 13B:
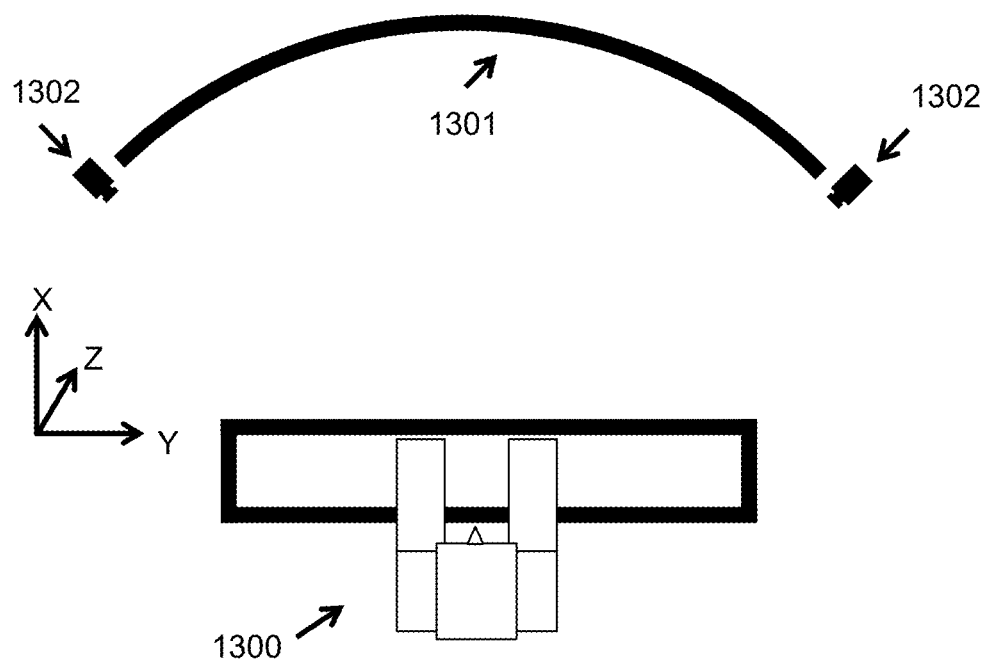
FIG. 13B illustrates a top down view of a screen upon which a user could view a prioritized volume rendered image.

FIG. 13B illustrates a top down view of a screen upon which a user could view a prioritized volume rendered image. 1300 illustrates a radiologist sitting at a desk. 1301 illustrates a curved screen, which is curved in the x-z plane. 1302 illustrates an eye tracking camera. The eye tracking camera is useful because it can track where the user is looking on the screen, which can then alter the appearance of the image as described in 62/985,363. In some embodiments, however, the eye tracking can serve as an input for prioritizing an imaging feature. In some embodiments, a monitor comprises a first screen wherein a first curvature is in a first plane and a second curvature is in a second plane. This is referred to as a dual curved monitor. In some embodiments, conventional practice of radiology is performed on the dual curved monitor.

Figure 14:
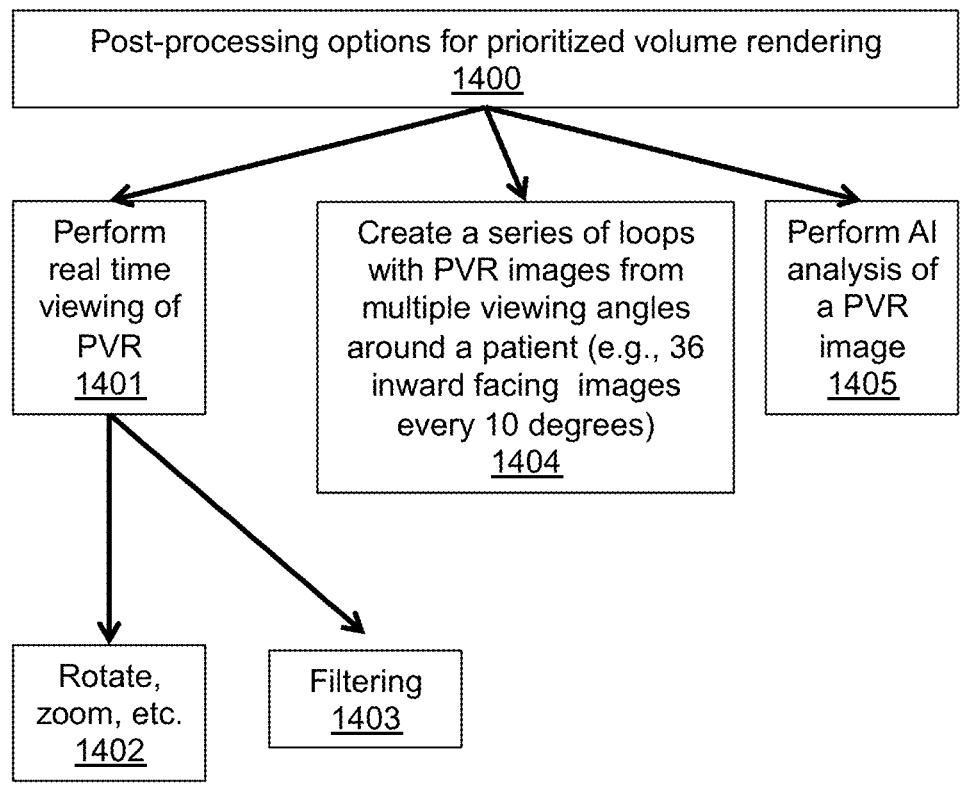
FIG. 14 illustrates post-processing options for prioritized volume rendering.

FIG. 14 illustrates post-processing options for prioritized volume rendering. 1400 illustrates post-processing options for prioritized volume rendering. 1401 illustrates performing real time viewing of prioritized volume rendering. 1402 illustrates viewing options, which a user can perform in real time, which includes altering the following: view point(s); viewing angles; interocular distance; convergence points; and, visual representation adjustment logic. Additionally, 1403 illustrates the option of filtering. The steps of filtering would include: selecting a set of imaging features based on their priority level that is desired to be viewed; and subtracting the remaining imaging features which do not meet the filtering criteria. For example, the user could select "display all voxels with PL of 10 only", or "display all voxels with PL of 9 and 10" or "hide voxels in between viewing perspective and voxels with PL of 10" and so on. 1404 illustrates creating a cine comprised of multiple images that a user could play, fast forward, rewind, etc. An example would be prioritized volume rendering of the cerebral vasculature. The basilar tip could be the imaging feature with the highest priority level. The more peripherally located vasculature would be the lower priority level imaging features. A 360 degree rotation could be accomplished with a view from every 10 degrees, starting with and anterior view point and viewing angle looking posterior, then after 90 degrees proceeding to a right lateral view point and viewing angle looking toward the left side of the patient, then after another 90 degrees proceeding to a posterior view point and viewing angle looking anterior, then after another 90 degrees proceeding to a left lateral view point and looking toward the right side of the patient and then returning to a starting position. This loop is therefore an example of a post-processing option for prioritized volume rendering. Next, in 1405 is an example of inputting the prioritized volume rendering images into an artificial intelligence algorithm for analysis. It is possible that inputting a processed image that the accuracy of an artificial intelligence algorithm be improved.

Figure 15:
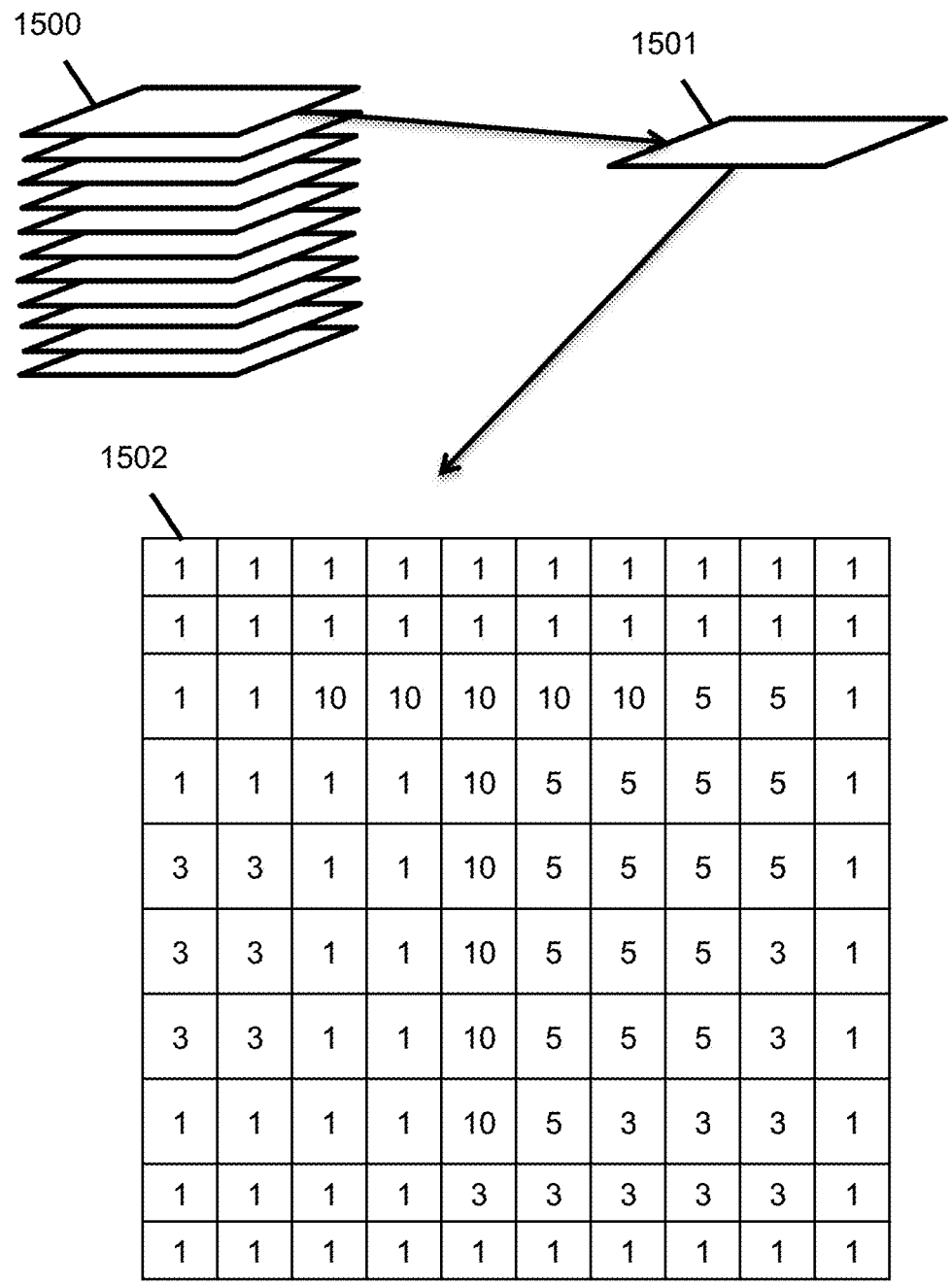
FIG. 15 illustrates an example assignment of priority levels to pixels within a slice.

FIG. 15 illustrates an example assignment of priority levels to pixels within a slice. In this example, priority levels are assigned on a 10-point scale with 10 being the highest priority level and 1 being the lowest priority level. Please note that priority is distinctly different from contrast property, which is commonly used for filtering and segmentation. This will be discussed further in subsequent figures. 1500 illustrates a stack of slices. 1501 illustrates a single slice at the top of the stack. 1502 illustrates wherein each pixel (or corresponding voxel, which is a 3D pixel element) in slice 1501 is assigned a priority level. Note that the PL level map corresponds to the data unit map, such that each (x, y, z) voxel will have a data unit and a PL.

FIG. 16A illustrates a 10×10 matrix of data units of a contrast enhanced computed tomography (CT) scan of a carotid artery. The 10×10 dataset is simulated to look like a contrast enhanced computed tomography (CT) scan with a good bolus and axial image of the carotid artery lumen with a dissection flap. Each number in this 10×10 matrix represents a Hounsfield Unit.

FIG. 16B illustrates prioritizing item(s) based on manual selection. Note that the PL level map corresponds to the data unit map, such that each (x, y, z) voxel will have a data unit and a PL. For illustrative purposes, there will be many different gray scales (depending on Hounsfield unit and window/leveling), but only 2 priority levels. Please note that in this example, priority levels are assigned manually based on user preference. These preference include, but are not limited to the following: x,y,z location(s) of item(s); contrast property (e.g., Hounsfield Units); random user assignment; arbitrary manual assignment; human determined selection strategy; artificial intelligence assignment; or, any combination thereof. In this example, a single x, y, z voxel is given a human assignment of a priority level of 10. All other voxels are given a human assignment of a priority level of 1. At subsequent time points, the prioritized values could change. This patent's process would be improve visualization of prioritized voxels that might not be as well noticed through current processes. through the total imaging volume. An example wherein this could be useful would be if a user was viewing axial images and identified a spot of interest in the anatomy and subsequently wanted this spot to be viewed during a subsequent volume rendered viewing strategy. For example, this spot could be the superior most aspect of a tumor and used as a landmark for volume rendering viewing. It is important to note the benefit of this PL driven viewing technique in that it allows one to visualize deeper structures of interest unhindered by more superficial structures of non interest while rotating, zooming, etc. Specifically, no matter what viewing angle is selected, the structures with a high PL can be seen. The user can then have a series of commands to further enhance viewing. For example, the user could select "display all voxels with PL of 10 only", or "display all voxels with PL of 9" or "hide voxels in between viewing perspective and voxels with PL of 10" and so on.

Figure 17:
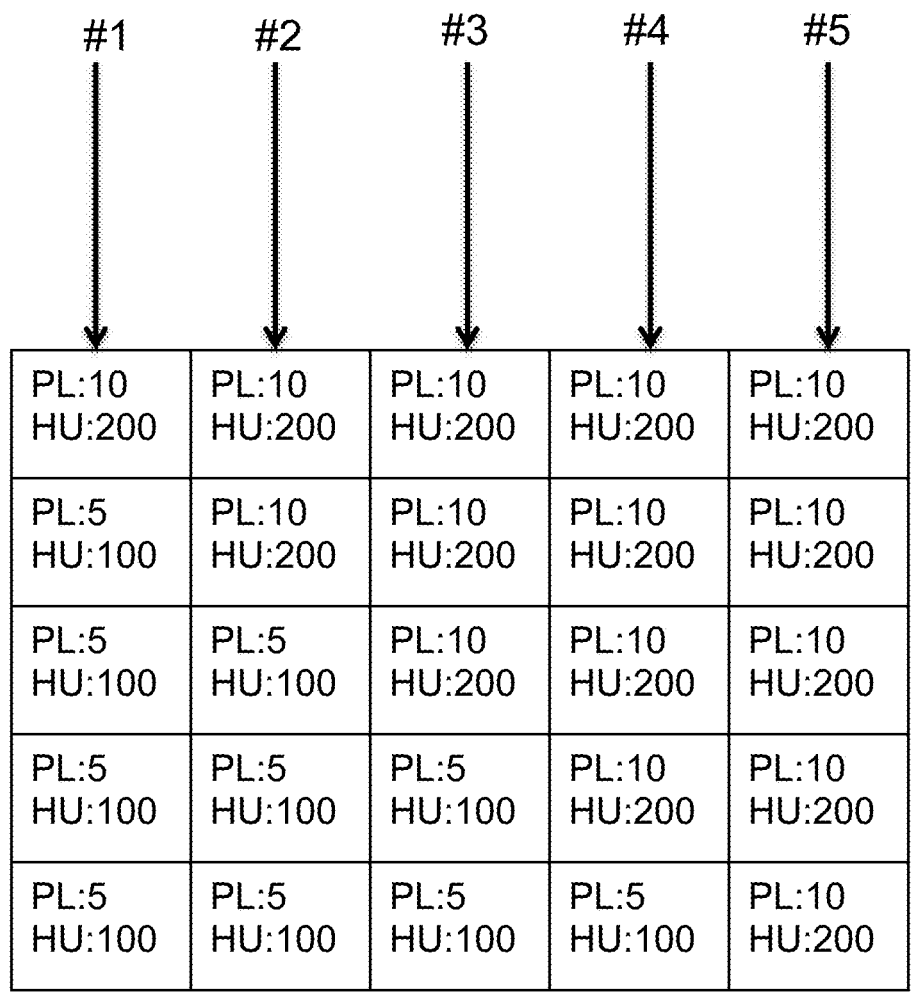
FIG. 17 illustrates the visualization augmentation strategies in the scenario wherein visual cues are provided based on the thickness of the item(s).

FIG. 17 illustrates the visualization augmentation strategies in the scenario wherein visual cues are provided based on the thickness of the item(s). In this illustration, simulated data is shown wherein priority level (PL) is assigned based on Hounsfield Units (HU). In this scenario, when a line is drawn from the viewing perspective to column #1, the first voxel encountered has PL 10 and HU 200. The remaining four voxels have PL 5 and HU 100. When a line is drawn from the viewing perspective to column #2, the first two voxels encountered have PL 10 and HU 200. The remaining three voxels have PL 5 and HU 100. When a line is drawn from the viewing perspective to column #3, the first three voxels encountered have PL 10 and HU 200. The remaining two voxels have PL 5 and HU 100. When a line is drawn from the viewing perspective to column #4, the first four voxels encountered have PL 10 and HU 200. The remaining voxel has PL 5 and HU 100. When a line is drawn from the viewing perspective to column #5, the all 5 voxels in this column have PL 10 and HU 200. Thus, the thickness of the PL 10 and HU 200 varies within the 3D volume. Thus, visual augmentation strategies are implemented to communicate this variable thickness to the user. The visual augmentation strategies include, but not limited to the following: alter contrast property (e.g., change gray scale, change color, etc.) of the prioritized item(s) to improve visualization of the prioritized item(s); perform dynamic viewing (e.g., sequentially showing and hiding of a prioritized item such that it blinks to improve its visualization); and, performing voxel manipulation (e.g., increase size of voxel(s) comprising the prioritized item(s). One example wherein this may be useful is for the dentist who wants to view a 3D image, but have depth information regarding the thickness of the enamel. Color-coding areas of thinning of enamel below a user specified threshold will expedite viewing over cross-sectional measurements. Another example where this may be useful is for the diagnostic radiologist who is trying to view a subtle fracture presenting as an oblique crack in a bone. Or alternatively, looking for endosteal scalloping of a bone tumor which lives inside the bone and thins a portion of the surface, but would not change the surface anatomy of the bone.

FIG. 18A illustrates which voxel of the three voxels is displayed based on a first Priority Level (PL) assignment. In this scenario, a window/level setting is set as 30/30. This means that Hounsfield Units (HU) of 30 are mid gray. Hounsfield units of +15 or less are black. Hounsfield Units of +45 or higher are white. 1800 illustrates a first voxel with PL of 1 and HU of −90. Under the window/level setting of 30/30, this first voxel 1800 would be displayed black on a 2D slice. 1801 illustrates a second voxel with PL of 5 and HU of 30. Under the window/level setting of 30/30, this second voxel 1801 would be displayed as mid-gray on a 2D slice. 1802 illustrates a third voxel with PL of 10 and HU of 100. Under the window/level setting of 30/30, this third voxel 1802 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1803 is illustrated and one of the group of the first voxel 1800, the second voxel 1801 and the third voxel 1802 will be displayed. The question of "which contrast is displayed?" 1804 is answered and in this scenario, the voxel with the highest PL will be displayed, which is the third voxel 1802 with PL of 10, which is white as shown in 1805.

FIG. 18B illustrates which voxel of the three voxels is displayed based on a second Priority Level (PL) assignment. In this scenario, a window/level setting is set as 30/30. This means that Hounsfield Units (HU) of 30 are mid gray. Hounsfield units of +15 or less are black. Hounsfield Units of +45 or higher are white. 1806 illustrates a first voxel with PL of 1 and HU of −90. Under the window/level setting of 30/30, this first voxel 1806 would be displayed black on a 2D slice. 1807 illustrates a second voxel with PL of 10 and HU of 30. Under the window/level setting of 30/30, this second voxel 1807 would be displayed as mid-gray on a 2D slice. 1808 illustrates a third voxel with PL of 5 and HU of 100. Under the window/level setting of 30/30, this third voxel 1808 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1809 is illustrated and one of the group of the first voxel 1806, the second voxel 1807 and the third voxel 1808 will be displayed. The question of "which contrast is displayed?" 1810 is answered and in this scenario, the voxel with the highest PL will be displayed, which is the second voxel 1807 with PL of 10, which is gray as shown in 1811.

FIG. 18C illustrates which voxel of the three voxels is displayed based on a third Priority Level (PL) assignment. In this scenario, a window/level setting is set as 30/30. This means that Hounsfield Units (HU) of 30 are mid gray. Hounsfield units of +15 or less are black. Hounsfield Units of +45 or higher are white. 1811 illustrates a first voxel with PL of 10 and HU of −90. Under the window/level setting of 30/30, this first voxel 411 would be displayed black on a 2D slice. 1807 illustrates a second voxel with PL of 5 and HU of 30. Under the window/level setting of 30/30, this second voxel 1812 would be displayed as mid-gray on a 2D slice. 1808 illustrates a third voxel with PL of 1 and HU of 100. Under the window/level setting of 30/30, this third voxel 1813 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1814 is illustrated and one of the group of the first voxel 1811, the second voxel 1812 and the third voxel 1813 will 1811 with PL of 10, which is black as shown in 1811.

FIG. 19A illustrates a first visual representation adjustment logic based on Priority Level. In this scenario, a window/level setting is set as 30/30. This means that Hounsfield Units (HU) of 30 are mid gray. Hounsfield units of +15 or less are black. Hounsfield Units of +45 or higher are white. 1900 illustrates a first voxel with PL of 1 and HU of −90. Under the window/level setting of 30/30, this first voxel 1900 would be displayed black on a 2D slice. 1901 illustrates a second voxel with PL of 10 and HU of 30. Under the window/level setting of 30/30, this second voxel 1901 would be displayed as mid-gray on a 2D slice. 1902 illustrates a third voxel with PL of 5 and HU of 100. Under the window/level setting of 30/30, this third voxel 1902 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1903 is illustrated and one of the group of the first voxel 1900, the second voxel 1901 and the third voxel 1902 will be displayed. The question of "which contrast is displayed?" 1904 is answered and in this scenario, the voxel with the highest PL will be displayed, which is the second voxel 1901 with PL of 10. In accordance with U.S. Pat. No. 10,596,400, the assignment can be red as shown in 1905. This can serve to help the user better notice the prioritized voxels (such as looking for small tumors).

FIG. 19B illustrates a second visual representation adjustment logic based on Priority Level. In this scenario, a window/level setting is set as 30/30. This means that Hounsfield Units (HU) of 30 are mid gray. Hounsfield units of +15 or less are black. Hounsfield Units of +45 or higher are white. 1906 illustrates a first voxel with PL of 1 and HU of −90. Under the window/level setting of 30/30, this first voxel 1906 would be displayed black on a 2D slice. 1907 illustrates a second voxel with PL of 9 and HU of 30. Under the window/level setting of 30/30, this second voxel 1907 would be displayed as mid-gray on a 2D slice. 1908 illustrates a third voxel with PL of 5 and HU of 100. Under the window/level setting of 30/30, this third voxel 1908 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1909 is illustrated and one of the group of the first voxel 1906, the second voxel 1907 and the third voxel 1908 will be displayed. The question of "which contrast is displayed?" 1910 is answered and in this scenario, the voxel with the highest PL will be displayed, which is the second voxel 1902 with PL of 9. In accordance with U.S. Pat. No. 10,596,400, the assignment can be flashing gray as shown in 1911. This can serve to help the user better notice the prioritized voxels (such as looking for small tumors).

FIG. 19C illustrates a third visual representation adjustment logic based on Priority Level. In this scenario, a window/level setting is set as 30/30. This means that Hounsfield Units (HU) of 30 are mid gray. Hounsfield units of +15 or less are black. Hounsfield Units of +45 or higher are white. 1912 illustrates a first voxel with PL of 1 and HU of −90. Under the window/level setting of 30/30, this first voxel 1912 would be displayed black on a 2D slice. 1913 illustrates a second voxel with PL of 8 and HU of 30. Under the window/level setting of 30/30, this second voxel 1913 would be displayed as mid-gray on a 2D slice. 1914 illustrates a third voxel with PL of 5 and HU of 100. Under the window/level setting of 30/30, this third voxel 1914 would be displayed as white on a 2D slice. It should be noted that the newly established PLs could be used for a slice-by-slice imaging technique wherein a first visual representation adjustment logic is utilized for a first group of PLs and a second visual representation adjustment logic is utilized for a second group of PLs, as is described in U.S. Pat. No. 10,596,400, which is incorporated by reference. It should be noted that in this scenario, a volume rendering approach is performed. This patent improves upon the current volume rendering approach (which utilizes only the data units in the voxels) because it also utilizes PLs to determine which voxel to display. In this scenario, the viewing perspective 1915 is illustrated and one of the group of the first voxel 1912, the second voxel 1913 and the third voxel 1914 will be displayed. The question of "which contrast is displayed?" 1916 is answered and in this scenario, the voxel with the highest PL will be displayed, which is the second voxel 1913 with PL of 8. The assignment can be gray as shown in 1911. This can serve to help the user better notice the prioritized voxels (such as looking for small tumors).

FIG. 20A illustrates a 10×10 matrix of data units of a contrast enhanced computed tomography (CT) scan of a carotid artery. The 10×10 dataset is simulated to look like a contrast enhanced computed tomography (CT) scan with a good bolus and axial image of the carotid artery lumen with a dissection flap. Each number in this 10×10 matrix represents a Hounsfield Unit.

FIG. 20B illustrates prioritizing item(s) based on item(s) property (e.g., contrast property, etc.). Note that the PL level map corresponds to the data unit map, such that each (x, y, z) voxel will have a data unit and a PL. For illustrative purposes, there will be many different gray scales (depending on Hounsfield unit and window/leveling), but only 3 priority levels. Please note that in this example, Hounsfield Units in the range of −60 to −100 are given priority level 1. Hounsfield Units in the range of +150 to +200 are given priority level 5. Hounsfield Units in the range of +30 to +60 are given priority level 10. The fat is given priority level 1. The contrast filling the carotid artery is given priority level 5. The dissection flap is given priority level 10. Current volume rendering techniques would show only the surface of the carotid artery and the internally located dissection flap would be missed. Maximum intensity projection (MIP) images would also miss the dissection flap. With this patent's prioritized volume rendering technique, the dissection flap would be given the highest priority level of 10 and would be displayed to the user. More specifically, no matter what the viewing angle would be, the voxels with the highest PL would be seen and the dissection flap would be seen. In some embodiments, segmentation of an imaging feature is first performed and prioritization levels within the segmented structure are second performed. For example, first segment the carotid artery and second assign priority levels within the segmented carotid artery. Finally, the segmented carotid artery wherein imaging feature(s) of the carotid artery are assigned priority levels can be viewed with prioritized volume rendering techniques.

FIG. 21A illustrates a 10×10 matrix of data units of a contrast enhanced computed tomography (CT) scan of a carotid artery. The 10×10 dataset is simulated to look like a contrast enhanced computed tomography (CT) scan with a good bolus and axial image of the carotid artery lumen with a dissection flap. Each number in this 10×10 matrix represents a Hounsfield Unit.

FIG. 21B illustrates prioritizing item(s) based on item(s) location (e.g., x,y,z location etc.). Note that the PL level map corresponds to the data unit map, such that each (x, y, z) voxel will have a data unit and a PL. For illustrative purposes, there will be many different gray scales (depending on Hounsfield unit and window/leveling), but only 2 priority levels. This 10×10 dataset is simulated to look like a contrast enhanced CT scan with a good bolus and axial image of the carotid artery lumen with a dissection flap. Please note that in this example, priority levels are assigned based on x,y,z coordinate (Note, this represents a slice of a given z). With this patent's prioritized volume rendering technique, the dissection flap would not be given the highest priority level of 10. Rather, the selected region based on x,y,z locations is given the highest priority level of 10. Within the prioritized volume, windowing and leveling could occur to improve visibility of the finding. At subsequent time points, the prioritized x,y,z value(s) could change. This process would be like moving a mobile, prioritized sub-volume through the total imaging volume. Techniques described in U.S. Pat. No. 9,980,691 and U.S. patent application Ser. No. 15/878,463. This prioritization strategy could be useful if it were known that a certain portion of the images were statistically more likely to have a pathologic finding. For example, the user could place a 3D cursor over finding suspicious for a brain aneurysm, manually assign all voxels or a specific subset of voxels inside of the 3D cursor a high priority level. Then, the user could move the cursor to a different spot and assign another set of voxels a high priority level. Then, after assigning the priority levels, the user could rotate, zoom, converge, and view the entire volume in a volume rendering process with superb visualization of the structure(s) of interest as indicated by the 3D cursor. It is important to note the benefit of this PL driven viewing technique in that it allows one to visualize deeper structures of interest unhindered by more superficial structures of non interest while rotating, zooming, etc.

FIG. 22A illustrates a 10×10 matrix of data units of a contrast enhanced computed tomography (CT) scan of a carotid artery. The 10×10 dataset is simulated to look like a contrast enhanced computed tomography (CT) scan with a good bolus and axial image of the carotid artery lumen with a dissection flap. Each number in this 10×10 matrix represents a Hounsfield Unit.

FIG. 22B illustrates prioritizing item(s) based on manual selection. Note that the PL level map corresponds to the data unit map, such that each (x, y, z) voxel will have a data unit and a PL. For illustrative purposes, there will be many different gray scales (depending on Hounsfield unit and window/leveling), but only 2 priority levels. Please note that in this example, priority levels are assigned based on user preference. These preference include, but are not limited to the following: x,y,z location(s) of item(s); contrast property (e.g., Hounsfield Units); random user assignment; arbitrary manual assignment; human determined selection strategy; artificial intelligence assignment; or, any combination thereof. In this example, a single x, y, z voxel is given a human assignment of a priority level of 10. All other voxels are given a human assignment of a priority level of 1. At subsequent time points, the prioritized values could change. This patent's process would be improve visualization of prioritized voxels that might not be as well noticed through current processes. through the total imaging volume. An example wherein this could be useful would be if a user was viewing axial images and identified a spot of interest in the anatomy and subsequently wanted this spot to be viewed during a subsequent volume rendered viewing strategy. For example, this spot could be the superior most aspect of a tumor and used as a landmark for volume rendering viewing. It is important to note the benefit of this PL driven viewing technique in that it allows one to visualize deeper structures of interest unhindered by more superficial structures of non interest while rotating, zooming, etc. Specifically, no matter what viewing angle is selected, the structures with a high PL can be seen. The user can then have a series of commands to further enhance viewing. For example, the user could select "display only imaging features with PL of 10", or "display all voxels with PL of 9 or "hide voxels in between viewing perspective and voxels with PL of 10" and so on.

FIG. 23A illustrates a 10×10 matrix of data units of a contrast enhanced computed tomography (CT) scan of a carotid artery. The 10×10 dataset is simulated to look like a contrast enhanced computed tomography (CT) scan with a good bolus and axial image of the carotid artery lumen with a dissection flap. Each number in this 10×10 matrix represents a Hounsfield Unit.

FIG. 23B illustrates prioritizing item(s) based on artificial intelligence (e.g., machine learning algorithm determines priority). In this illustration, an artificial intelligence algorithm determines the priority of the x, y, z voxels. Note that the PL level map corresponds to the data unit map, such that each (x, y, z) voxel will have a data unit and a PL. For example, machine learning (e.g., neural networks, deep learning) algorithms may be used. For illustrative purposes, there will be many different gray scales (depending on Hounsfield unit and window/leveling), but only 3 priority levels. This 10×10 dataset is simulated to look like a contrast enhanced CT scan with a good bolus and axial image of the carotid artery lumen with a dissection flap. Please note that in this example, the artificial intelligence algorithm determines PLs. Current volume rendering techniques would show only the surface of the carotid artery and the internally located dissection flap would be missed. Maximum intensity projection (MIP) images would also miss the dissection flap. With this patent's prioritized volume rendering technique, the dissection flap would be given the highest priority level (as assigned by the artificial intelligence algorithm) of 10 and would be preferentially displayed to the user. Note that the user could view the prioritized volume rendering under a first artificial intelligence algorithm assignment during a first review and then review the prioritized volume rendering under a second artificial intelligence algorithm during a second review.

Figure 24:
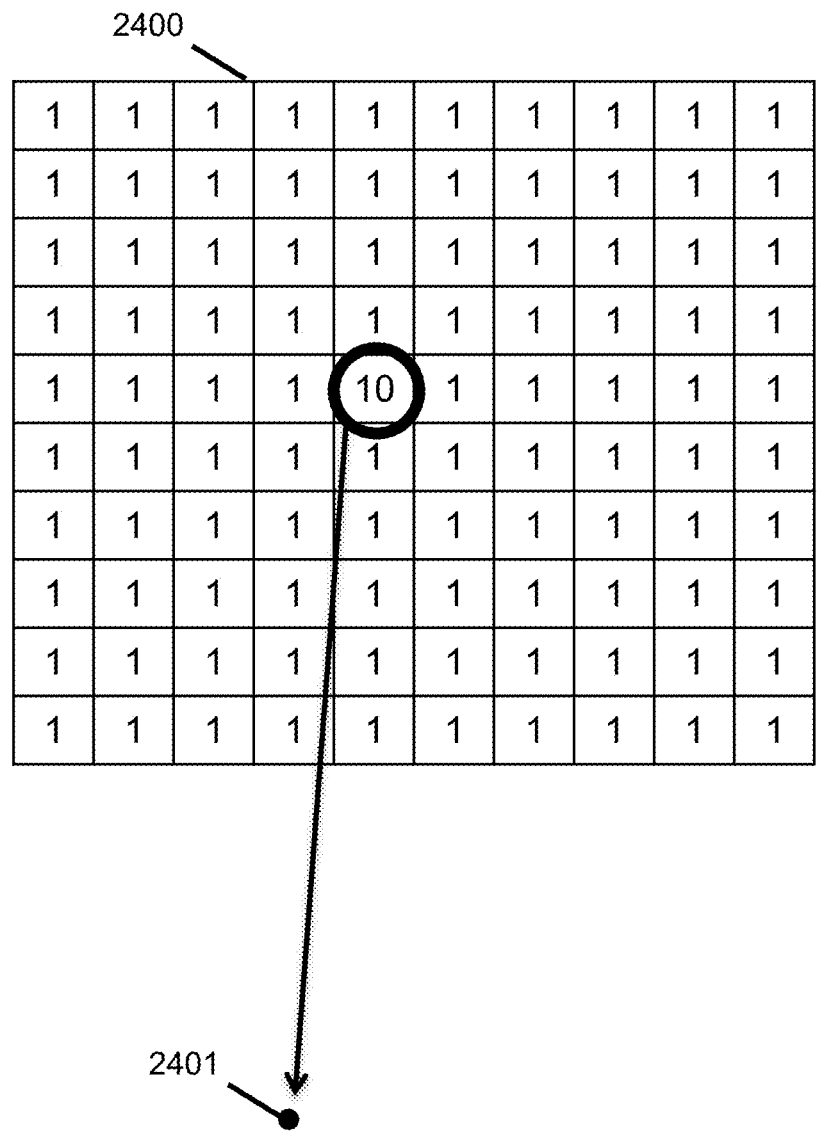
FIG. 24 illustrates an example of an imaging feature, which is a zero-dimensional object or point.

FIG. 24 illustrates an example of an imaging feature, which is a zero-dimensional object or point. An example PL dataset is shown in 2400. Note that x, y, z data points from a 3D dataset can be displayed as a point or as a voxel depending on the way that the data is processed. In this example, it is projected as a single voxel 2400. In this example, a single voxel is given a PL of 10 and all other 99 voxels from the 3D dataset are assigned a PL of 1. If the user selects "display only voxels priority level 10", then only a single voxel will be displayed as shown in 2401.

Figure 25:
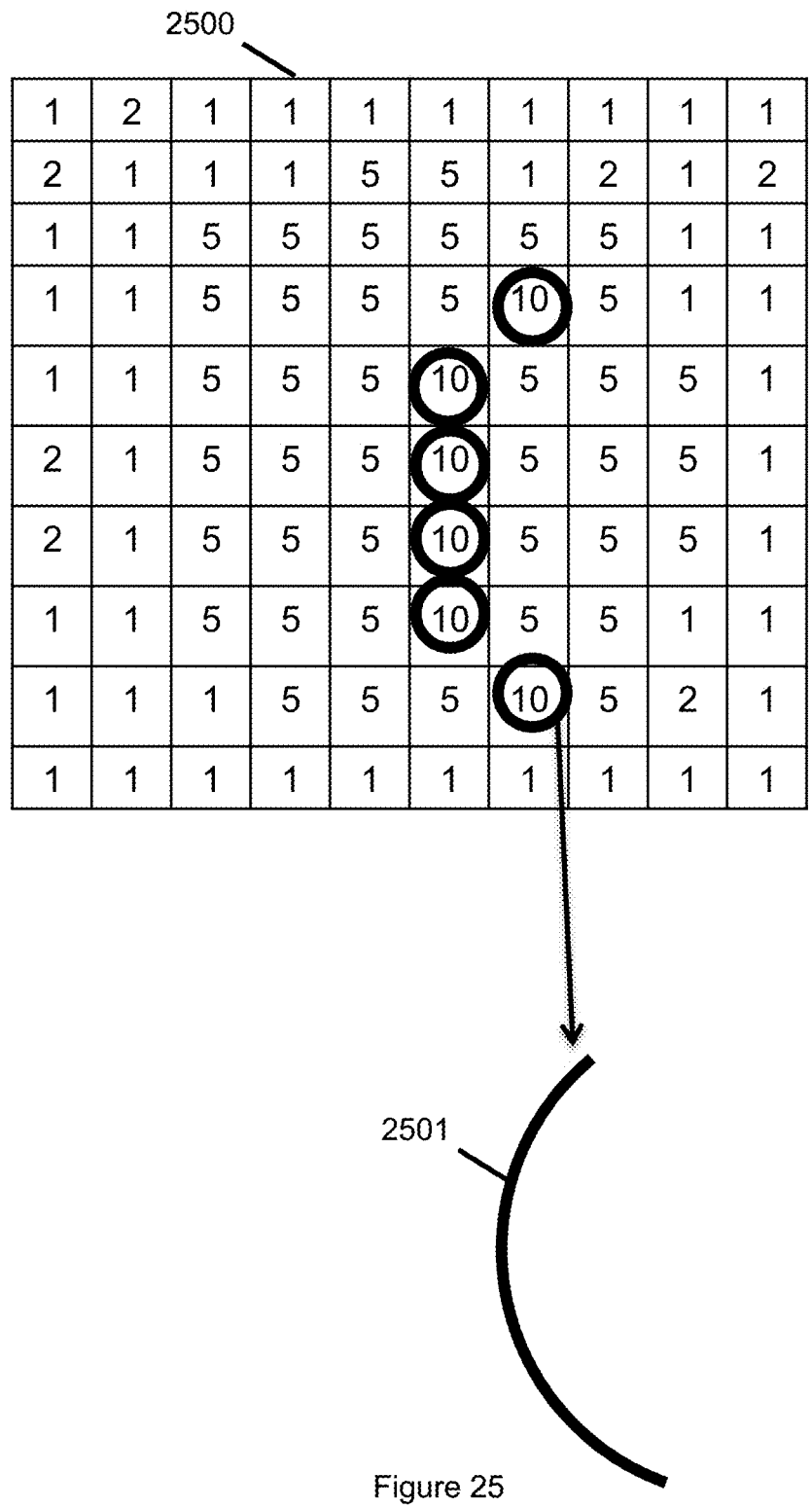
FIG. 25 illustrates another example of an imaging feature, which is a curvilinear line.

FIG. 25 illustrates another example of an imaging feature, which is a curvilinear line. An example PL dataset is shown in 2500. Note that multiple x,y,z data points from a 3D dataset can be displayed as a line or as a volume (comprised of multiple voxel) depending on the way that the data is processed. In this example, it is projected as a line, as shown by 2501.

Figure 26:
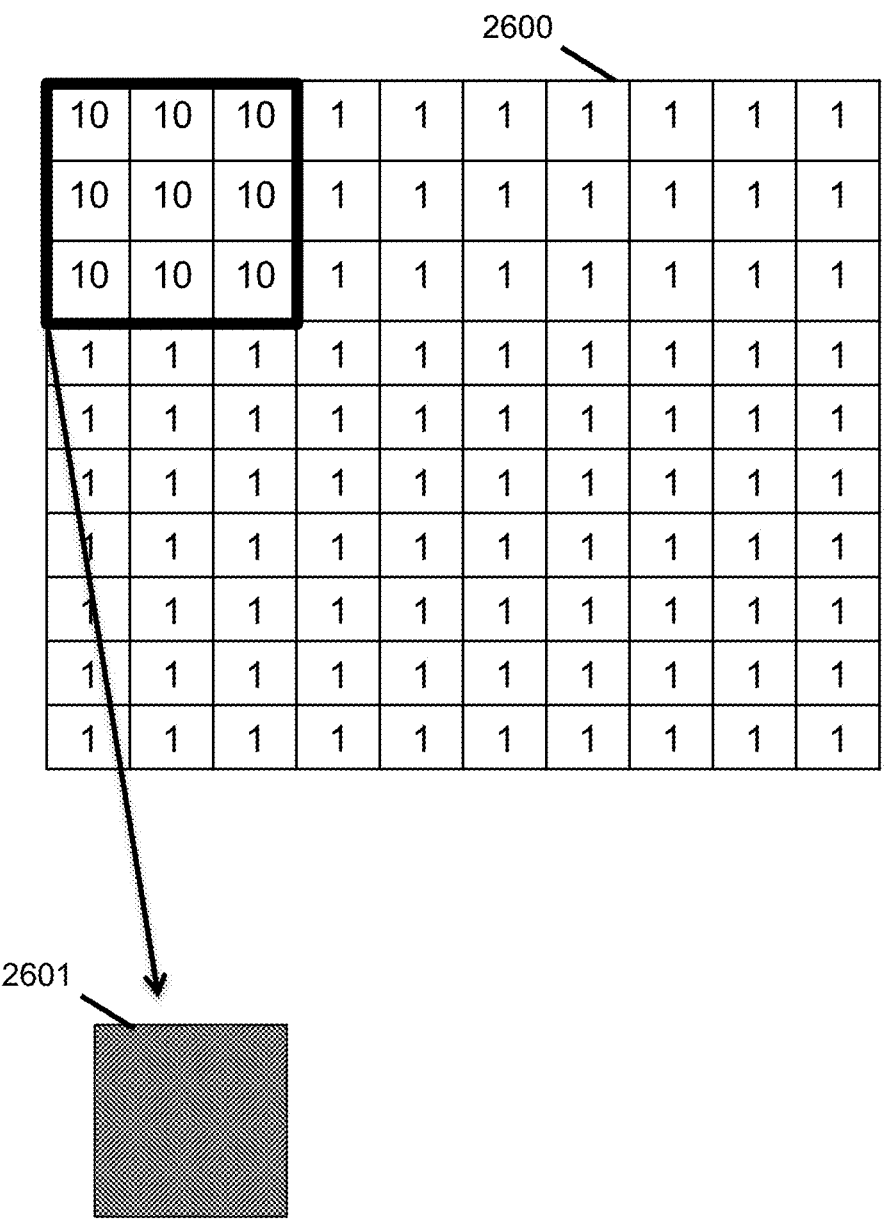
FIG. 26 illustrates another example of an imaging feature, which is a two-dimensional object.

FIG. 26 illustrates another example of an imaging feature, which is a two-dimensional object. An example PL dataset is shown in 2600. Note that multiple x,y,z data points from a 3D dataset can be displayed as a two-dimensional object (e.g., slice, plane, surface, etc.), as illustrated in 2601.

Figure 27:
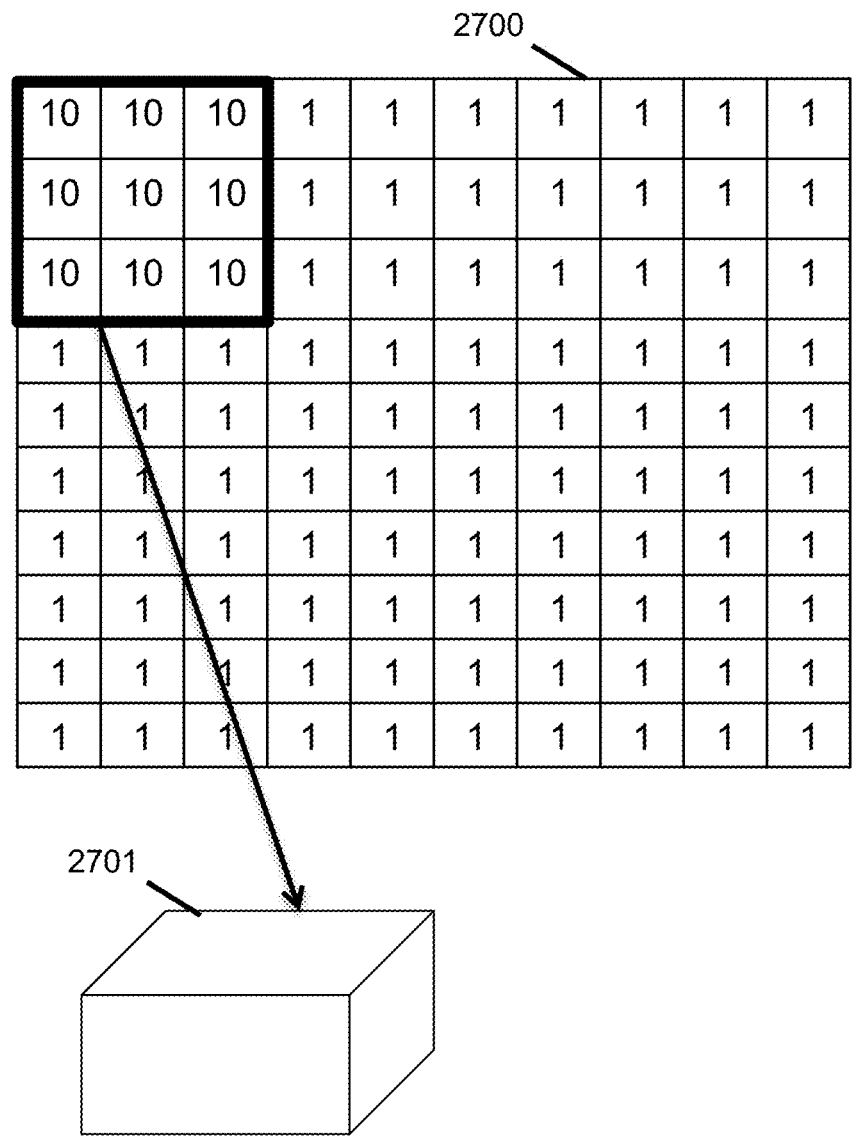
FIG. 27 illustrates another example of an imaging feature, which is a three-dimensional object.

FIG. 27 illustrates another example of an imaging feature, which is a three-dimensional object. An example PL dataset is shown in 2700. Note that multiple x,y,z data points from a 3D dataset can be displayed as a three-dimensional object or sub-volume (comprised of multiple voxels). In this example, it is projected as a three-dimensional object, as illustrated in 2701.

Figure 28:
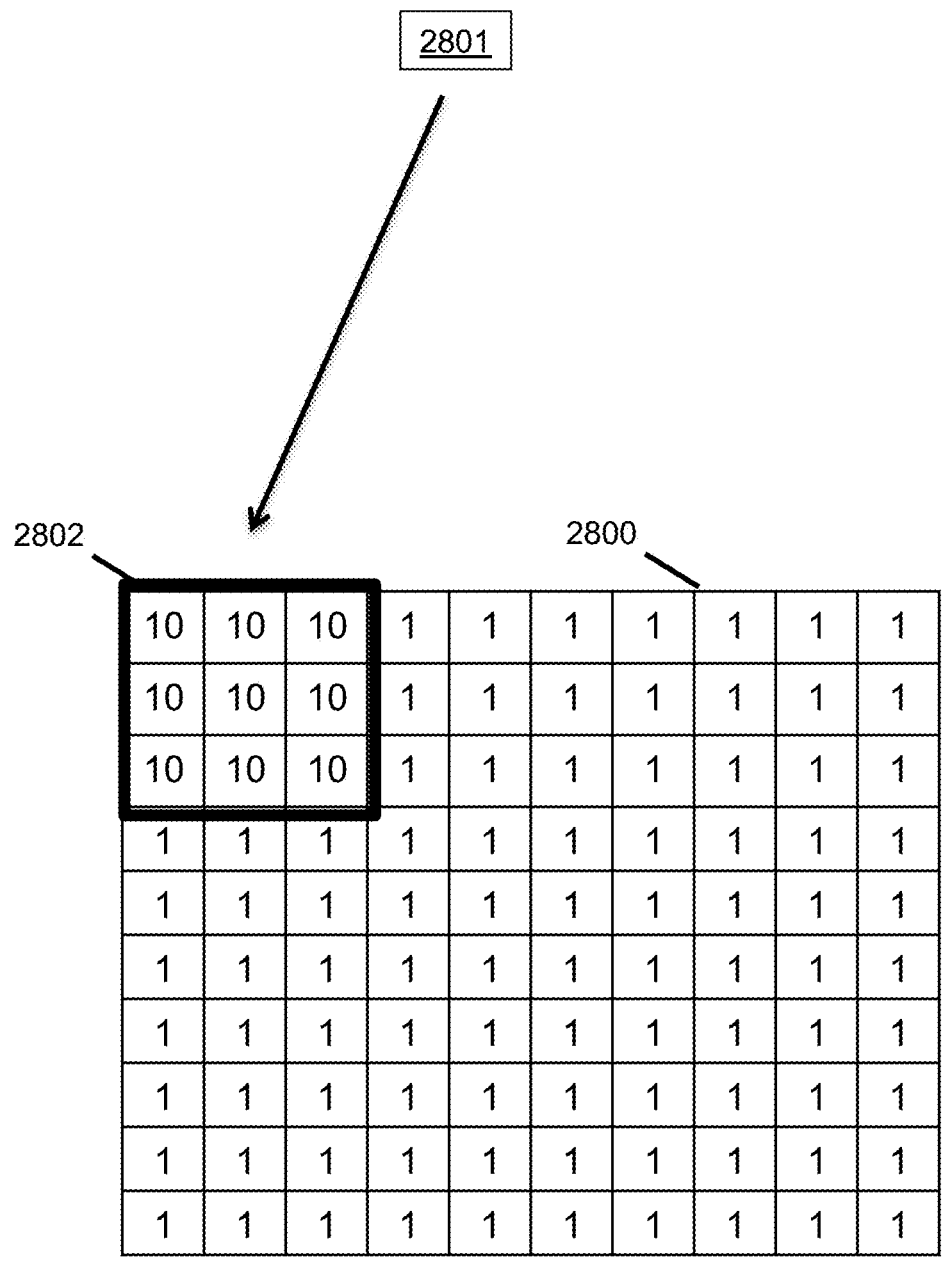
FIG. 28 illustrates the visualization augmentation strategies in the scenario wherein there are no non-prioritized imaging features in between the viewing perspective(s) and the prioritized item(s).

FIG. 28 illustrates the visualization augmentation strategies in the scenario wherein there are no non-prioritized items in between the viewing perspective(s) and the prioritized item(s). Note that when a line is drawn from the viewing perspective 2801 to the 3D volume 2800, the very first item that it runs into is the prioritized item 2802; therefore, there are no non-prioritized items in between the viewing perspective and the voxels. In this scenario, the visualization augmentation strategies include, but are not limited to the following: adjusting the contrast property (e.g., altering the gray scale appearance, adding color); perform dynamic viewing (e.g., sequentially showing and hiding of a prioritized item such that it blinks to improve its visualization); and, performing voxel manipulation (e.g., increase size of voxel(s) comprising the prioritized imaging feature(s).)

Figure 29:
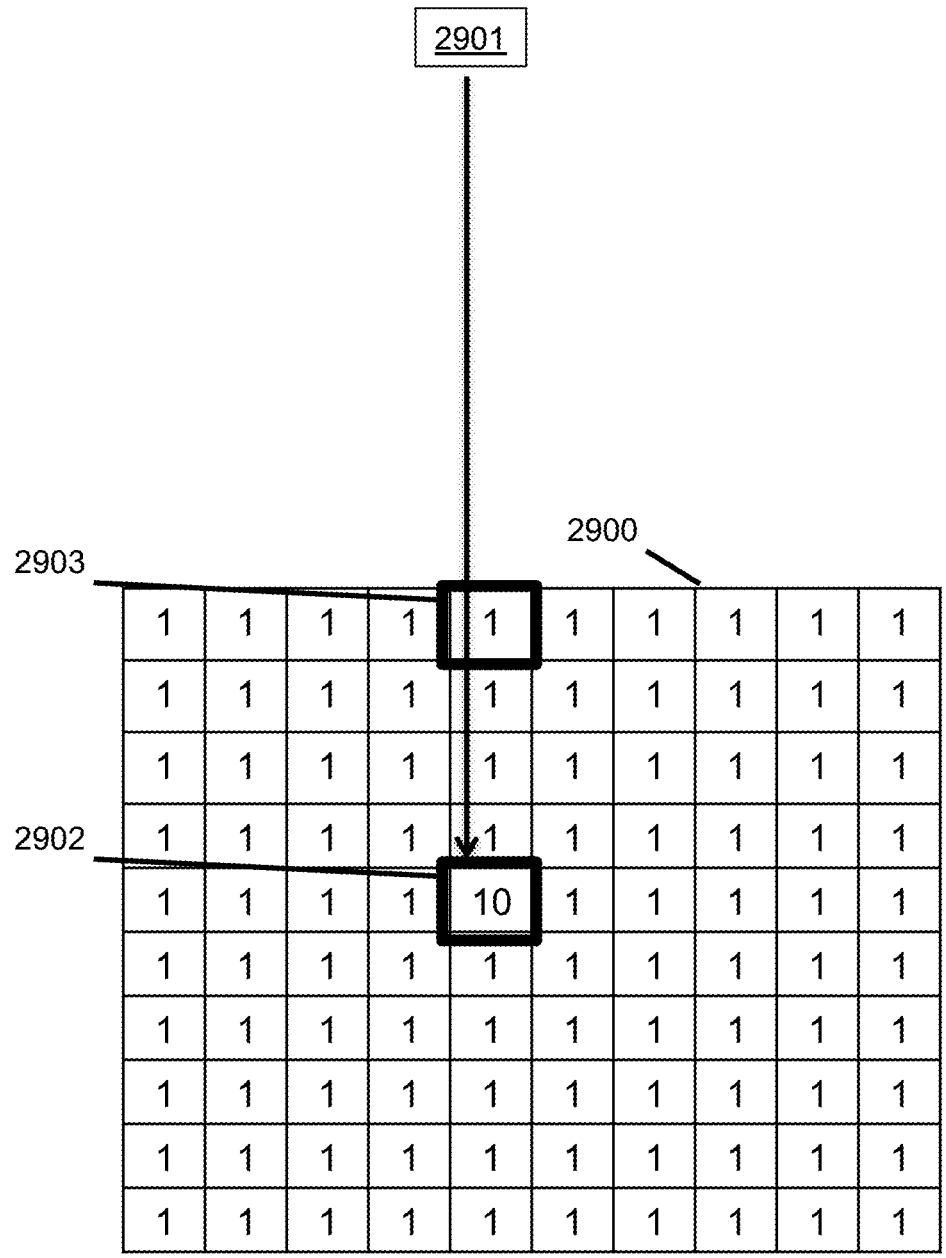
FIG. 29 illustrates the visualization augmentation strategies in the scenario wherein there are non-prioritized items in between the viewing perspectives and the prioritized item(s).

FIG. 29 illustrates the visualization augmentation strategies in the scenario wherein there are non-prioritized items in between the viewing perspectives and the prioritized item(s). Note that when a line is drawn from the viewing perspective 2901 to the imaging feature 2902 of the 3D volume 2900, the very first item that it runs into is a non-prioritized imaging feature 2903; therefore, there are non-prioritized items in between the viewing perspective and the voxels. In this scenario, the visualization augmentation strategies include, but are not limited to the following: complete preferential display of higher prioritized item(s) over lower prioritized items (i.e., any time that a non-prioritized item(s) is in between the viewing perspective(s) and prioritized item(s), the non-prioritized item is hidden); or, partial preferential display of higher prioritized item(s) over lower prioritized items (e.g., use dynamic filtration such that the prioritized item(s) are displayed for a greater fraction of time than the non-prioritized item(s)). Note that if partial preferential display of higher prioritized items is performed over lower prioritized items, the extent at which the higher prioritized items are displayed over the lower prioritized items can be varies based on many factors, which include, but are not limited to the following: relative locations; relative assigned priorities; relative contrast properties; window/level settings; or, combinations thereof.

Figure 30A:
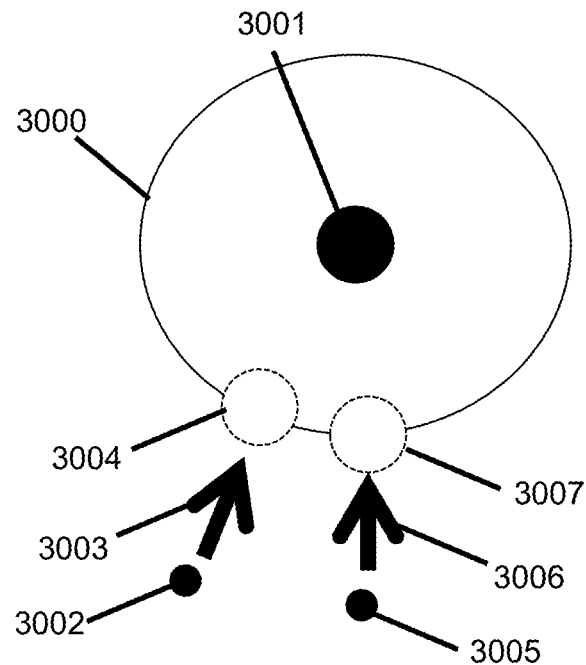
FIG. 30A illustrates prioritized voxels during an initial viewing perspective.

FIG. 30A illustrates prioritized voxels during an initial viewing perspective. 3000 illustrates a first layer of voxels (e.g., normal cortex of vertebral body), which is assigned a low priority level. 3001 illustrates a second group of voxels (e.g., cancerous lesion within the center of the vertebral body), which is assigned a high priority level. 3002 illustrates an initial left eye view point. 3003 illustrates an initial left eye viewing angle. 3004 illustrates non-prioritized voxels to cause improved viewing of the second group of voxels 3001. In this example, the non-prioritized voxels 3004 are rendered transparent. 3005 illustrates an initial right eye view point. 3006 illustrates an initial right eye viewing angle. 3007 illustrates non-prioritized voxels to cause improved viewing of the second group of voxels 3001. In this example, the non-prioritized voxels 3007 are rendered transparent.

Figure 30B:
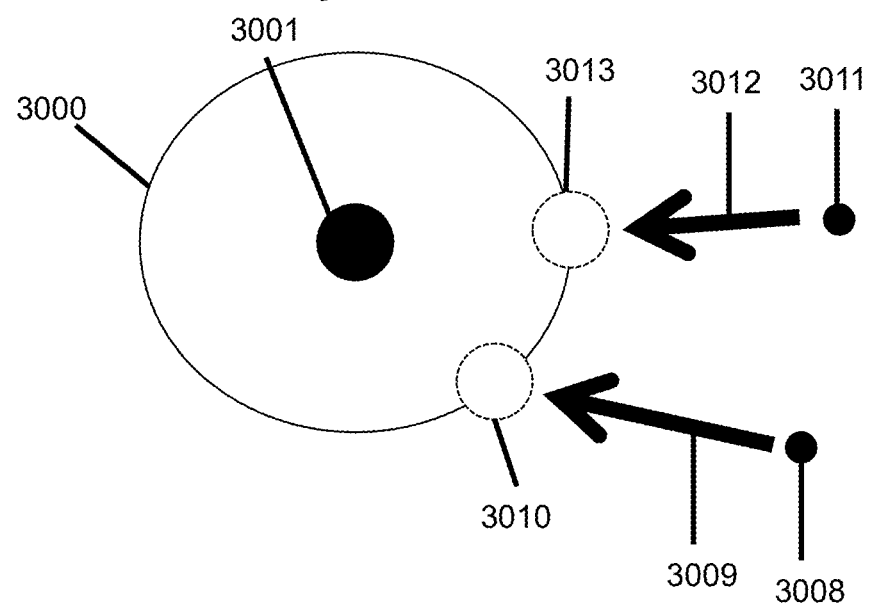
FIG. 30B illustrates prioritized voxels during a subsequent viewing perspective.

FIG. 30B illustrates prioritized voxels during a subsequent viewing perspective. 3000 illustrates a first layer of voxels (e.g., normal cortex of vertebral body), which is assigned a low priority level. 3001 illustrates a second group of voxels (e.g., cancerous lesion within the center of the vertebral body), which is assigned a high priority level. 3008 illustrates an subsequent left eye view point. 3009 illustrates an subsequent left eye viewing angle. 3010 illustrates non-prioritized voxels to cause improved viewing of the second group of voxels 3001. In this example, the non-prioritized voxels 3010 are rendered transparent. 3011 illustrates a subsequent right eye view point. 3012 illustrates a subsequent right eye viewing angle. 3013 illustrates non-prioritized voxels to cause improved viewing of the second group of voxels 3001. In this example, the non-prioritized voxels 3013 are rendered transparent. Note that as the view points and viewing angles have changed, a different set of voxels are rendered transparent. This is useful because it allows the user to see the prioritized bad imaging feature (e.g., tumor) unhindered by low priority imaging features no matter what view points are used.

Figure 31A:
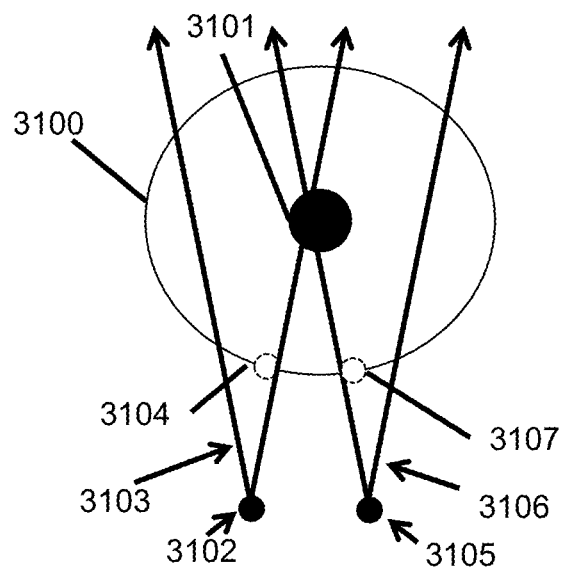
FIG. 31A illustrates prioritized voxels during viewing with a first viewing setting.

FIG. 31A illustrates prioritized voxels during viewing with a first viewing setting. 3100 illustrates a first layer of voxels (e.g., normal cortex of vertebral body), which is assigned a low priority level. 3101 illustrates a second group of voxels (e.g., cancerous lesion within the center of the vertebral body), which is assigned a high priority level. 3102 illustrates the initial left eye view point. 3103 illustrates the initial left eye field of view. 3104 illustrates the initial low-prioritized voxels hidden from image derived from the left eye field of view. 3105 illustrates the initial right eye view point. 3106 illustrates the initial right eye field of view. 3107 illustrates the initial low-prioritized voxels hidden from image derived from right eye field of view.

Figure 31B:
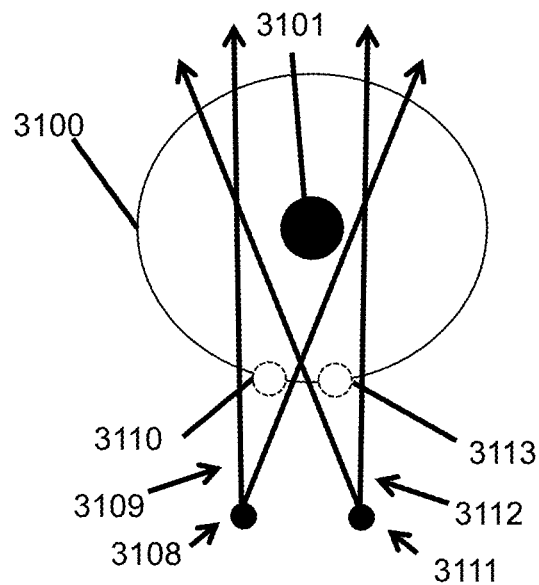
FIG. 31B illustrates prioritized voxels during viewing with a subsequent viewing setting of convergence.

FIG. 31B illustrates prioritized voxels during viewing with a subsequent viewing setting of convergence. See U.S. Pat. No. 9,349,183 for additional details on convergence, which is incorporated by reference. 3100 illustrates a first layer of voxels (e.g., normal cortex of vertebral body), which is assigned a low priority level. 3101 illustrates a second group of voxels (e.g., cancerous lesion within the center of the vertebral body), which is assigned a high priority level. 3108 illustrates the subsequent left eye view point. 3109 illustrates the subsequent left eye field of view. 3110 illustrates the subsequent low-prioritized voxels hidden from image derived from left eye field of view. 3111 illustrates the subsequent right eye view point. 3112 illustrates the subsequent right eye field of view. Note that convergence has now been implemented. 3113 illustrates the subsequent low-prioritized voxels hidden from image derived from the right eye field of view. Note that as the convergence has been implemented, a different set of voxels are rendered transparent. This is useful because it allows the user to see the prioritized bad imaging feature (e.g., tumor) unhindered by low priority imaging features no matter what viewing angle or interocular distance is used.

Figure 32A:
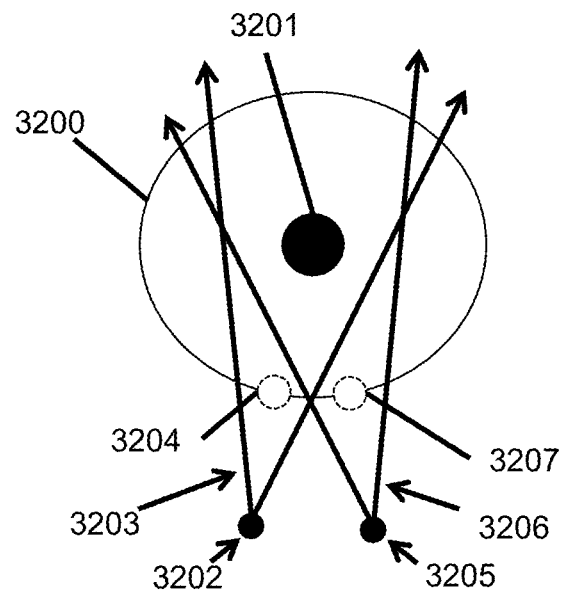
FIG. 32A illustrates prioritized voxels during viewing with a first intraocular distance.

FIG. 32A illustrates prioritized voxels during viewing with a first intraocular distance. 3200 illustrates a first layer of voxels (e.g., normal cortex of vertebral body), which is assigned a low priority level. 3201 illustrates a second group of voxels (e.g., cancerous lesion within the center of the vertebral body), which is assigned a high priority level. 3202 illustrates the initial left eye view point. 3203 illustrates the initial left eye field of view. 3204 illustrates the initial low-prioritized voxels hidden from image derived from the left eye field of view. 3205 illustrates the initial right eye view point. 3206 illustrates the initial right eye field of view. 3207 illustrates the initial low-prioritized voxels hidden from image derived from right eye field of view.

Figure 32B:
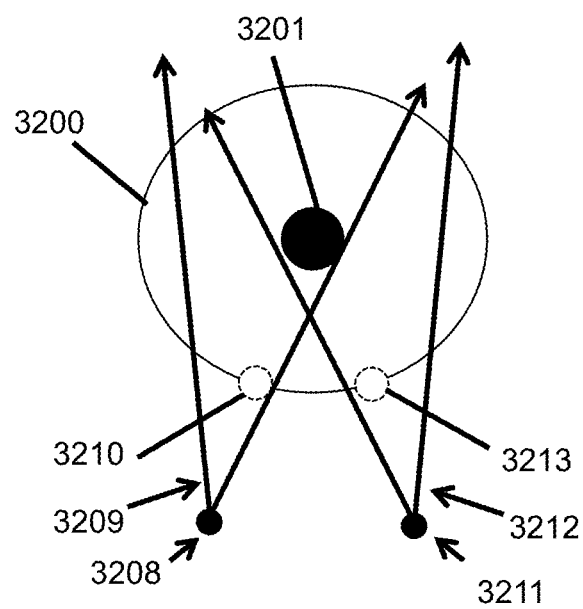
FIG. 32B illustrates prioritized voxels during viewing with a subsequent intraocular distance.

FIG. 32B illustrates prioritized voxels during viewing with a subsequent intraocular distance. 3200 illustrates a first layer of voxels (e.g., normal cortex of vertebral body), which is assigned a low priority level. 3201 illustrates a second group of voxels (e.g., cancerous lesion within the center of the vertebral body), which is assigned a high priority level. 3208 illustrates the subsequent left eye view point. 3209 illustrates the subsequent left eye field of view. 3210 illustrates the subsequent low-prioritized voxels hidden from image derived from left eye field of view. 3211 illustrates the subsequent right eye view point. Note that the interocular distance between the left eye view point 3209 and the right eye view point 3211 has changed. 3212 illustrates the subsequent right eye field of view. 3213 illustrates the subsequent low-prioritized voxels hidden from image derived from the right eye field of view. Note that as the interocular distance changes, a different set of voxels are rendered transparent. This is useful because it allows the user to see the prioritized bad imaging feature (e.g., tumor) unhindered by low priority imaging features no matter what viewing angle or interocular distance is used.

Figure 33A:
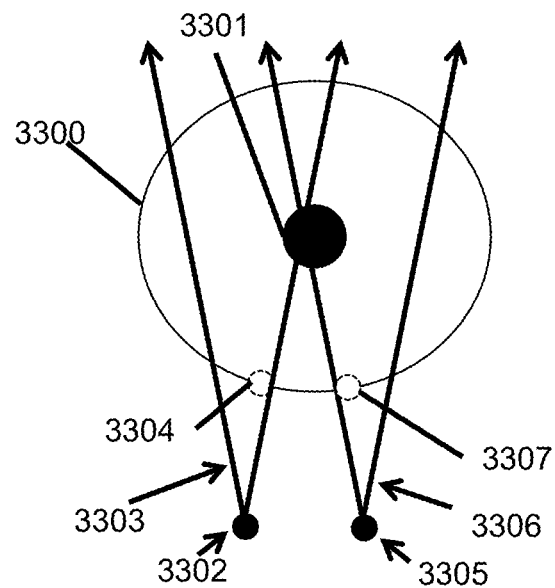
FIG. 33A illustrates prioritized voxels during initial field of view.

FIG. 33A illustrates prioritized voxels during initial field of view. 3300 illustrates a first layer of voxels (e.g., normal cortex of vertebral body), which is assigned a low priority level. 3301 illustrates a second group of voxels (e.g., cancerous lesion within the center of the vertebral body), which is assigned a high priority level. 3302 illustrates the initial left eye view point. 3303 illustrates the initial left eye field of view. 3304 illustrates the initial low-prioritized voxels hidden from image derived from the left eye field of view. 3305 illustrates the initial right eye view point. 3306 illustrates the initial right eye field of view. 3307 illustrates the initial low-prioritized voxels hidden from image derived from right eye field of view.

Figure 33B:
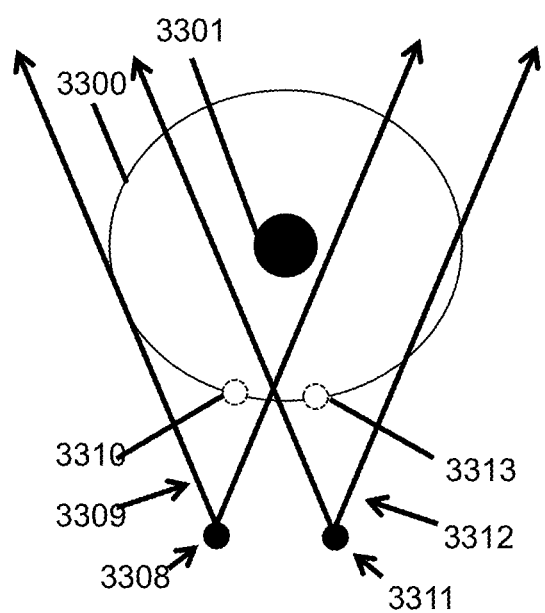
FIG. 33B illustrates prioritized voxels during a subsequent field of view.

FIG. 33B illustrates prioritized voxels during a subsequent field of view. 3300 illustrates a first layer of voxels (e.g., normal cortex of vertebral body), which is assigned a low priority level. 3301 illustrates a second group of voxels (e.g., cancerous lesion within the center of the vertebral body), which is assigned a high priority level. 3308 illustrates the subsequent left eye view point. 3309 illustrates the subsequent left eye field of view. Note that the subsequent left eye field of view 3309 has changed as compared to the initial left eye field of view 3303. 3310 illustrates the subsequent low-prioritized voxels hidden from image derived from left eye field of view. 3311 illustrates the subsequent right eye view point. 3312 illustrates the subsequent right eye field of view. Note that the subsequent right eye field of view 3312 has changed as compared to the initial left eye field of view 3306. 3313 illustrates the subsequent low-prioritized voxels hidden from image derived from the right eye field of view. Note that as the field of view changes, a different set of voxels are rendered transparent. This is useful because it allows the user to see the prioritized bad imaging feature (e.g., tumor) unhindered by low priority imaging features no matter what viewing angle or interocular distance is used. Other viewing options such as those described in U.S. Pat. No. 8,384,771, which is incorporated by reference, can also be implemented.

FIG. 34A illustrates an axial CT scan of a thoracic vertebral and left eye and right eye view points and left and right eye viewing angles for depth 3-dimensional viewing. 3400 illustrates an axial CT image of a thoracic vertebrae. 3401 illustrates a sclerotic lesion within the center of the vertebral body. 3402 illustrates a left eye view point. 3403 illustrates a left eye viewing angle. 3404 illustrates a right eye view point. 3405 illustrates a right eye viewing angle. Please see U.S. Pat. No. 8,384,771, which is incorporated by reference for details on depth-3-dimensional viewing.

FIG. 34B illustrates an extended reality headset. 3406 illustrates the extended reality headset. The image on the left eye display and the image on the right eye display are determined by the geometry from FIG. 34A. Note that the images illustrate the surface of the vertebral bodies, but do not show the sclerotic lesion 3401 in the center of the vertebral body.

FIG. 34C illustrates an axial CT scan of a thoracic vertebral and left eye and right eye view points and left and right eye viewing angles for depth 3-dimensional viewing. 3400 illustrates an axial CT image of a thoracic vertebrae. 3401 illustrates a sclerotic lesion within the center of the vertebral body. 3402 illustrates a left eye view point. 3403 illustrates a left eye viewing angle. 3404 illustrates a right eye view point. 3405 illustrates a right eye viewing angle. 3407 illustrates a cluster of high attenuation Hounsfield units corresponding to cortical bone, which are located along the left eye viewing angle in between the left eye view point and the sclerotic lesion 3401. 3408 illustrates a cluster of high attenuation Hounsfield units corresponding to cortical bone, which are located along the right eye viewing angle in between the right eye view point and the sclerotic lesion 3401. Please see U.S. Pat. No. 8,384,771, which is incorporated by reference for details on depth-3-dimensional viewing.

FIG. 34D illustrates an extended reality headset with images acquired through prioritized volume rendering, which overcomes the limitation a deeper structure being hidden by superficial structures. 3409 illustrates the extended reality headset. 3410 illustrates the sclerotic lesion of interest in the left eye display, which is located within the central portion of the vertebral body. 3411 illustrates the sclerotic lesion of interest in the right eye display, which is located within the central portion of the vertebral body. Since prioritized volume rendering shows deeper structures 3401 (which are higher priority than the superficial structures 3407 and 3408), image analysis is improved.

Figure 35:
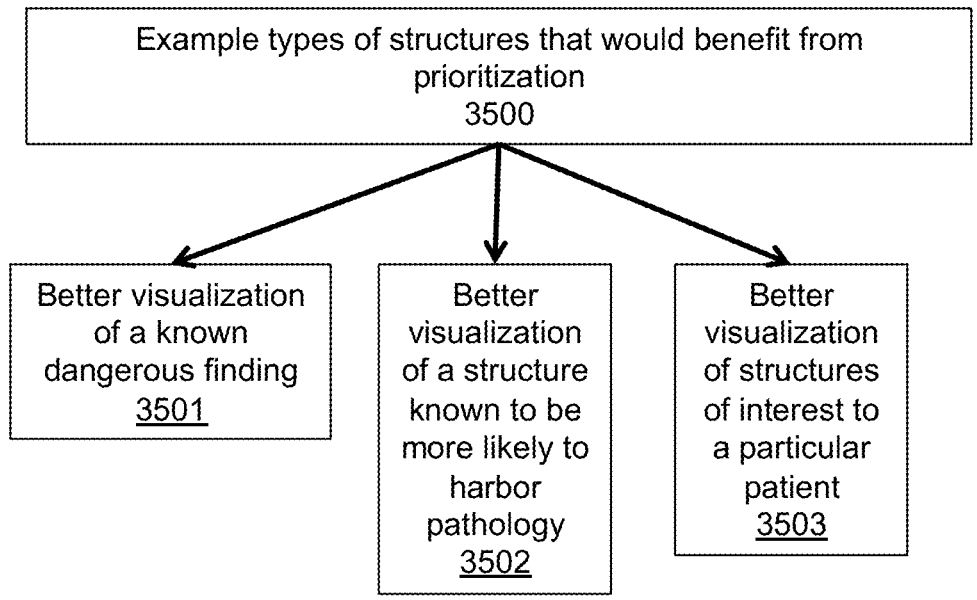
FIG. 35 illustrates the types of structures that would benefit from prioritized viewing.

FIG. 35 illustrates the types of structures that would benefit from prioritized viewing. 3500 illustrates example types of structures that would benefit from prioritization. 3501 illustrates better visualization of a known dangerous finding. For example, if a patient has a 1 cm spiculated pulmonary nodule, prioritized volume rendering can be performed and lead to better visualization and improved image analysis and diagnosis. 3502 illustrates better visualization of a structure known to be more likely to harbor pathology. Certain structures in the body are more likely to harbor pathology than others. For example, the meniscus of a knee is a common spot for trauma. Therefore, prioritized volume rendering of the meniscus of a knee can be performed and lead to improved image analysis and diagnosis. 3503 illustrates better visualization of structures of interest to a particular patient. Certain patients may have a history which suggests pathology of a particular anatomic structure. For example, the patient may have physical examination findings indicative of a rotator cuff injury. Therefore, the rotator cuff structures (which can be isolated via segmentation techniques) can be given prioritized volume rendering. This will allow the user to view the rotator cuff from many angles unhindered by more superficial structures of non-interest while still having context.

Figure 36:
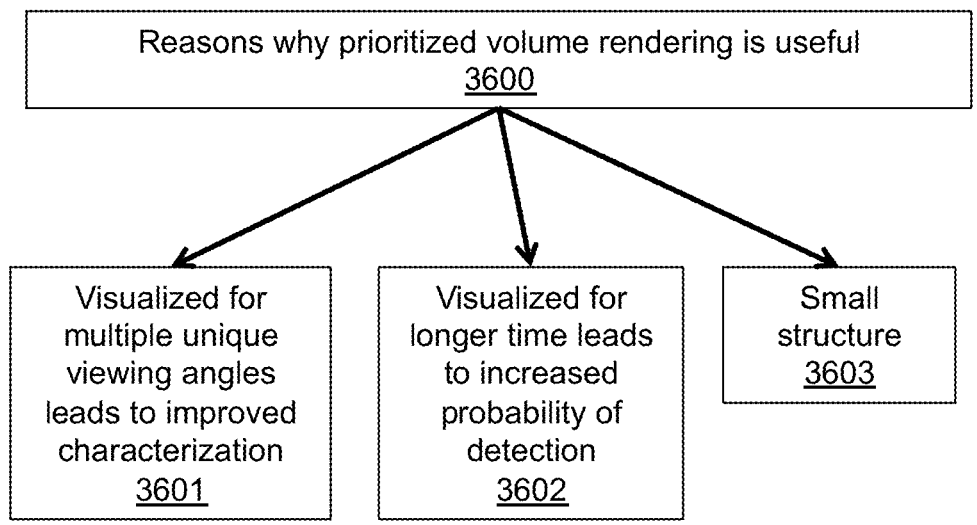
FIG. 36 illustrates reasons why prioritized volume rendering is useful.

FIG. 36 illustrates reasons why prioritized volume rendering is useful. 3600 illustrates scenarios wherein prioritized volume rendering is useful. 3601 illustrates an important scenario wherein visualizing a lesion from multiple unique viewing angles leads to improved characterization. An example of this is a brain aneurysm. It is important to view a brain aneurysm from multiple angles so a user can see the brain aneurysm neck, dome, branch vessels, orientation, etc. Viewing of a brain aneurysm from multiple angles can be limited due to the fact that the brain aneurysm is a deep structure and there are multiple superficial structures that are in the way. Thus, by performing prioritized volume rendering, the visualization of a brain aneurysm can be improved, since depending on the viewing angle, some (but not all) of the more superficial structures (e.g., cerebral vascular branches of non-interest) are rendered transparent. 3602 illustrates an important scenario in imaging, which is more effectively accomplished using prioritized volume rendering. The more chances a radiologist has to detect a lesion, the higher probability of detection. Therefore, using prioritized volume rendering can help allow a dangerous lesion to be viewed for a longer time period. Consider back to FIG. 1. The prioritized volume rendering allows a longer time of looking at the tumor. 3603 illustrates a small structure. Prioritized volume rendering improves upon conventional volume rendering by providing improved visualization of small structures because they will not be blocked by more superficial structures.

Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
    assigning a first imaging feature within a 3D dataset a first priority level;
    assigning a second imaging feature within the 3D dataset a second priority level wherein the first imaging feature is different from the second imaging feature and wherein the first priority level is different from the second priority level;
    comparing the first priority level of the first imaging feature within the 3D dataset with the second priority level of the second imaging feature within the 3D dataset; and in a scenario wherein a viewing perspective is aligned with the first imaging feature and the second imaging feature wherein the first imaging feature is located in between the viewing perspective and the second imaging feature, performing rendering of the first imaging feature if the first priority level is higher than the second priority level; and performing rendering of the second imaging feature if the second priority level is higher than the first priority level.

2. The method of claim 1 further comprising wherein imaging features comprises at least one of the group of: a single voxel; a group of voxels comprising a single contiguous segmented structure; and, a group of voxels comprising anatomically distinct structures.

3. The method of claim 1 of displaying the 3D dataset on one of the group comprising:
a 2D monitor;
an extended reality display; and
a dual-curved monitor wherein the top portion of the dual-curved monitor curves inwards towards the user, the bottom portion of the dual-curved monitor curves inwards towards the user; the left portion of the dual-curved monitor curves inward towards the user; and the right portion of the dual-curved monitor curves inward towards the user.

4. The method of claim 1 further comprising wherein assigning priority levels to imaging features is performed based on the contrast property of the imaging features.

5. The method of claim 1 further comprising wherein the assigning priority levels to imaging features is performed based on the location of the imaging features.

6. The method of claim 1 further comprising wherein the assigning priority levels to imaging features is performed based on the level of dangerous level of an imaging feature.

7. The method of claim 1 further comprising wherein the assigning priority levels to imaging features is performed based on the probability of an imaging feature harboring pathology.

8. The method of claim 1 further comprising wherein the assigning priority levels to imaging features is performed based on the imaging features of interest as determined by the checklist item of the radiologist.

9. The method of claim 1 further comprising wherein the assigning priority levels to imaging features is performed based on manual selection.

10. The method of claim 1 further comprising wherein the assigning priority levels to imaging features is performed based on an artificial intelligence algorithm.

11. The method of claim 1 further comprising wherein a first visual representation adjustment logic is applied to the first imaging feature and a second visual representation adjustment logic is applied to the second imaging feature wherein the first visual representation adjustment logic is different from the second visual representation adjustment logic.

12. The method of claim 1 further comprising dynamic priority level assignment wherein:
the first imaging feature with the first priority level within the 3D dataset has the first priority level during a first time epoch and wherein the
first imaging feature with the first priority level within the 3D dataset has the first priority level during a first time epoch.

13. The method of claim 1 further comprising performing voxel manipulation of the imaging feature with the higher assigned priority level to improve visualization of the imaging feature with the higher assigned priority level.

14. The method of claim 1 further comprising utilizing a visualization augmentation strategy comprising altering the contrast property of the imaging feature with the higher assigned priority level to improve visualization of the prioritized imaging feature.

15. The method of claim 1 of performing rendering of the second imaging feature further comprising wherein the first imaging feature is hidden during the rendering of the second imaging feature in at least one of the group comprising: the first imaging feature is completely hidden from visualization; the first imaging feature is partially hidden from visualization; and, the first imaging feature is hidden in a dynamic fashion wherein at a first time point the first imaging feature is hidden and at a second time point the first imaging feature is not hidden.

16. The method of claim 1 further comprises implementing advanced visualization strategies comprising: rotating the 3D dataset; altering the viewing angle;
zooming; converging; changing interocular distance; and, altering the field of view.

17. An apparatus comprising:
a processor;
a display;
a non-transitory memory having computer-executable instructions stored thereupon which, when executed by the processor, cause the processor to perform:
assigning a first imaging feature within a 3D dataset a first priority level; and
assigning a second imaging feature within the 3D dataset a second priority level wherein the first imaging feature is different from the second imaging feature and wherein the first priority level is different from the second priority level;
comparing the first priority level of the first imaging feature within the 3D dataset with the second priority level of the second imaging feature within the 3D dataset; and
in a scenario wherein a viewing perspective is aligned with the first imaging feature and the second imaging feature wherein the first imaging feature is located in between the viewing perspective and the second imaging feature,
performing rendering of the first imaging feature if the first priority level is higher than the second priority level; and
performing rendering of the second imaging feature if the second priority level is higher than the first priority level.

18. A non-transitory computer readable medium having computer readable code thereon for image processing, the medium comprising:
instructions for assigning a first imaging feature within a 3D dataset a first priority level;
instructions for assigning a second imaging feature within the 3D dataset a second priority level wherein the first imaging feature is different from the second imaging feature and wherein the first priority level is different from the second priority level;
comparing the first priority level of the first imaging feature within the 3D dataset with the second priority level of the second imaging feature within the 3D dataset; and
in a scenario wherein a viewing perspective is aligned with the first imaging feature and the second imaging feature wherein the first imaging feature is located in between the viewing perspective and the second imaging feature, performing rendering of the first imaging feature if the first priority level is higher than the second priority level; and performing rendering of the second imaging feature if the second priority level is higher than the first priority level.

* * * * *